US009629935B2

(12) United States Patent
Yeh

(10) Patent No.: US 9,629,935 B2
(45) Date of Patent: Apr. 25, 2017

(54) METHOD FOR QUANTIFYING THE CHARACTERISTICS OF AN OBJECT TREATED WITH A CONTRAST AGENT

(71) Applicant: James Shue-Min Yeh, London (GB)

(72) Inventor: James Shue-Min Yeh, London (GB)

( * ) Notice: Subject to any disclaimer, the term of this patent is extended or adjusted under 35 U.S.C. 154(b) by 0 days.

(21) Appl. No.: 14/654,709

(22) PCT Filed: Dec. 20, 2013

(86) PCT No.: PCT/GB2013/053405
§ 371 (c)(1),
(2) Date: Jun. 22, 2015

(87) PCT Pub. No.: WO2014/096863
PCT Pub. Date: Jun. 26, 2014

(65) Prior Publication Data
US 2016/0199033 A1    Jul. 14, 2016

(30) Foreign Application Priority Data

Dec. 21, 2012  (GB) .................................. 1223328.4

(51) Int. Cl.
*G06K 9/00*    (2006.01)
*A61K 49/22*   (2006.01)
(Continued)

(52) U.S. Cl.
CPC .......... *A61K 49/227* (2013.01); *A61B 6/481* (2013.01); *A61B 6/486* (2013.01); *A61B 6/5217* (2013.01); *A61B 8/06* (2013.01); *A61B 8/481* (2013.01); *A61B 8/5223* (2013.01); *A61K 49/0017* (2013.01); *A61K 49/0034* (2013.01);
(Continued)

(58) Field of Classification Search
USPC .................................................. 382/128–134
See application file for complete search history.

(56) References Cited

U.S. PATENT DOCUMENTS

| 5,024,230 A * | 6/1991 | Lindstrom ........... A61B 5/0275 382/131 |
| 2005/0048539 A1 * | 3/2005 | Hyman .............. G01N 33/6896 435/6.11 |

(Continued)

OTHER PUBLICATIONS

International Search Report and Written Opinion dated Apr. 15, 2014 for International Application No. PCT/GB2013/053405, International Filing Date Dec. 20, 2013 consisting of 11 pages.
Correas et al: "Human Pharmacokinetics of a Perfluorocarbon Ultrasound Contrast Agent Evaluated with Gas Chromatography", Ultrasound in Medicine and Biologym Apr. 2, 2001, vol. 27, No. 4, pp. 565-570.

(Continued)

*Primary Examiner* — Alex Liew
(74) *Attorney, Agent, or Firm* — Christopher & Weisberg, P.A.

(57) ABSTRACT

The method comprises: a) receiving a plurality of imaging signals of the object over a period of time; b) measuring the signal intensity in each of the plurality of imaging signals corresponding to a point on the object; and c) curve fitting the measured signal intensity of the point on the object to a bi-exponential function comprising a first and a second exponential term, the first exponential term representing the decrease in concentration of the contrast agent which is free over time and the second exponential term representing a decrease in concentration of the contrast agent which is retained on the object over time.

30 Claims, 11 Drawing Sheets

(51) Int. Cl.

| | | |
|---|---|---|
| *A61B 8/06* | (2006.01) | |
| *G01R 33/56* | (2006.01) | |
| *A61B 6/00* | (2006.01) | |
| *A61B 8/08* | (2006.01) | |
| *G06T 7/00* | (2017.01) | |
| *A61K 49/00* | (2006.01) | |
| *A61K 49/16* | (2006.01) | |
| *A61K 49/18* | (2006.01) | |
| *A61B 5/055* | (2006.01) | |
| *A61B 5/02* | (2006.01) | |
| *G06F 19/00* | (2011.01) | |

(52) U.S. Cl.
CPC ...... *A61K 49/0058* (2013.01); *A61K 49/0082* (2013.01); *A61K 49/16* (2013.01); *A61K 49/1809* (2013.01); *A61K 49/221* (2013.01); *A61K 49/223* (2013.01); *G01R 33/5601* (2013.01); *G06T 7/0016* (2013.01); *A61B 5/02028* (2013.01); *A61B 5/055* (2013.01); *A61B 2576/023* (2013.01); *G06F 19/321* (2013.01); *G06T 2207/10088* (2013.01); *G06T 2207/10132* (2013.01); *G06T 2207/30104* (2013.01)

(56) References Cited

U.S. PATENT DOCUMENTS

| | | | | |
|---|---|---|---|---|
| 2006/0149479 | A1* | 7/2006 | Ma | A61B 5/0059 |
| | | | | 702/19 |
| 2007/0047786 | A1* | 3/2007 | Aklilu | G06K 9/6255 |
| | | | | 382/128 |
| 2008/0108894 | A1* | 5/2008 | Elgavish | G06T 7/0012 |
| | | | | 600/420 |
| 2010/0135566 | A1* | 6/2010 | Joanidopoulos | G06K 9/0014 |
| | | | | 382/133 |
| 2011/0257519 | A1* | 10/2011 | Bj?rnerud | A61B 5/055 |
| | | | | 600/431 |
| 2013/0022548 | A1* | 1/2013 | Bennett | A61K 49/12 |
| | | | | 424/9.3 |

OTHER PUBLICATIONS

Nilsson et al: "Biexponential Fitting of Diffusion-Ordered NMR Data: Practicalities and Limitations", Analytical Chemistry, May 2, 2006, vol. 78, No. 9, pp. 3040-3045.

Stokes et al: "Characterization of Restricted Difussion in Uni-and Multi-Lamellar Vesicles Using Short Distance iMQCs", Journal of Magnetic Resonance, Oct. 2, 2012, vol. 223, No. 2, pp. 31-40.

* cited by examiner

| Bubble population | Tissue | Parameters | WT | | | Esel KO | | | Difference between WT & Esel KO |
|---|---|---|---|---|---|---|---|---|---|
| | | | Mean ± SEM | Range | n | Mean ± SEM | Range | n | p |
| Freely circulating & retained bubbles | Myocardium | $R^2$ (Goodness of curve-fit) | 0.88 ± 0.03 | 0.7-0.96 | 12 | 0.87 ± 0.04 | 0.62-0.97 | 8 | 0.92 |
| Freely circulating bubbles | Myocardium | $A_f$ (AU) | 4 ± 0.7 | 0.2-8.2 | 12 | 5.4 ± 0.9 | 2-8.9 | 8 | 0.25 |
| | | $\lambda_f$ (/min) | 0.45 ± 0.08 | 0.14-1.12 | 12 | 0.5 ± 0.07 | 0.27-0.79 | 8 | 0.64 |
| | | bubble half-life $\left(\frac{Ln2}{\lambda_f}\right)$ (min) | 2.1 ± 0.3 | 0.6-5.1 | 12 | 1.6 ± 0.2 | 0.9-2.5 | 8 | 0.32 |
| Retained bubbles | Myocardium | $A_r$ (AU) | 2.3 ± 0.4 | 0.8-4.2 | 12 | 0.4 ± 0.1 | 0-1 | 8 | <0.005 |
| | | $\lambda_r$ (/min) | 0.13 ± 0.02 | 0.04-0.24 | 12 | 0.28 ± 0.06 | 0.05-0.63 | 8 | <0.05 |
| | | bubble half-life $\left(\frac{Ln2}{\lambda_r}\right)$ (min) | 6.9 ± 1.3 | 2.9-17.6 | 12 | 4.4 ± 1.3 | 1.1-14.3 | 8 | 0.22 |
| Retained bubbles | Myocardium | R20 (AU) | 0.46 ± 0.16 | 0.01-1.61 | 12 | 0.06 ± 0.03 | -0.01-0.24 | 8 | <0.05 |

FIG. 8
Table

METHOD FOR QUANTIFYING THE CHARACTERISTICS OF AN OBJECT TREATED WITH A CONTRAST AGENT

CROSS REFERENCE TO RELATED APPLICATION

This Application is a National Stage of, and claims priority to PCT Application No. PCT/GB2013/053405, filed 20 Dec. 2013, which claims priority of G.B. Patent Application No. 1223338.4, filed 21 Dec. 2012, the entirety of both of which are incorporated herein by reference.

FIELD OF INVENTION

A method of quantifying the characteristics of an object treated with a contrast agent is disclosed. More specifically, but not exclusively, such quantifying is disclosed where the contrast agent includes targeting microparticles which have been introduced into a subject.

BACKGROUND TO THE INVENTION

Contrast agents are microparticles detectable by imaging. The term "imaging" refers to detection using an imaging device, examples include but are not limited to, ultrasound or ultrasonic (US) imaging, magnetic resonance imaging (MRI), scintigraphy, single photon emission computed tomography (SPECT), positron emission tomography (PET), computed tomography (CT), X-ray imaging/fluoroscopy, fluorescence imaging, bioluminescence imaging, microscopy, optical methods, or multi-modal variants thereof.

Suitable contrast agents for (contrast enhanced) imaging depends on the nature of the imaging modality proposed, and vice versa. For example, gas-containing microparticles such as microbubbles may be used as contrast agents in US imaging; microparticles containing radionuclides (e.g., technetium-99m, thallium-201, iodine-123, iodine-131, gallium-67, indium-111, fluorine-18, carbon-11, nitrogen-13, oxygen-15, rubidium-82) may be used as contrast agents in scintigraphy, SPECT or PET; microparticles containing paramagnetic, superparamagnetic or ultrasuperparamagnetic materials (e.g., gadolinium (Gd), iron oxide, iron, platinum, manganese) may be used as contrast agents in MRI; microparticles containing radio-opaque materials (e.g., iodine, barium, metal) may be used in CT or X-ray imaging/fluoroscopy; microparticles containing fluorophores or fluorescent dye (e.g., fluorescein-5-isothiocyanate, rhodamine, 1,1'-dioctadecyl-3,3,3',3'-tetramethylindocarbocyanine perchlorate (DiI), 3,3'-dioctadecyloxacarbocyanine perchlorate (DiO)) may be used in fluorescence imaging/microscopy; microparticles containing enzyme substrates (e.g., that for luciferase) may be used in bioluminescence imaging. Contrast agents may be detectable by more than one imaging modality. For example, a microbubble with/without paramagnetic material may be detected by US imaging, MRI and microscopy.

The term "imaging signal" refers to the received signal in imaging, that is identified to represent that of a contrast agent or contrast agent plus another element (e.g., tissue or blood). The received signal includes, but is not limited to, the raw, radiofrequency or front data, data before/after coding or processing, image pixel data (or image), or the number/density/concentration of microparticles observed visually under microscopy.

The term "signal intensity" refers to the intensity or strength of the imaging signal, it may be used synonymously with similar terms such as (but not limited to), the signal amplitude, signal strength, signal power (eg signal voltage squared, signal audio loudness), signal decibel (dB), signal videointensity, signal videodensity (e.g., pixel intensity on an image in grey or other colour scale), or the number/density/concentration of microparticles observed visually under microscopy. Where appropriate, the image videodensity (e.g., pixel intensity) may be substantially linearised using a suitable function (e.g., decompression using an anti-log function).

Contrast agents which comprise molecular binding elements can be used in appropriate imaging modality/modalities for molecular imaging, for the detection of molecules of interest (target molecules). For example, US molecular imaging can be achieved using targeting microbubbles as contrast agents. Microbubbles are formed of a shell encapsulating a gas. The shell can be made of a lipid, protein or polymer. Microbubbles oscillate within an acoustic field producing signals appearing as bright spots on an US picture, thereby effecting US contrast enhancement. The microbubbles are sufficiently small to flow without obstruction through small blood vessels, rather like the way in which red blood cells flow. Targeting microbubbles have shells containing molecular binding elements, which bind to molecules of interest one wishes to detect. Thus, for example, when targeting microbubbles are introduced into the bloodstream, they circulate with the blood and attach and accumulate on and around the molecules of interest, detectable using US imaging. Non-targeting microbubbles can also be imaged using US molecular imaging.

The molecule of interest (target molecule, targeted molecule or molecular target) may be, but is not limited to, a molecule, protein, receptor, particle or cell (including that present on artificial/implanted materials, e.g., metal, polymer or drug on a coronary stent, prosthetic heart valve or closure device). The molecule of interest may be present on the surface of cells.

The molecule of interest may exist de-novo or may be introduced artificially into a subject or system.

The terms "contrast agent", "microparticle", "targeting microparticle", "microbubble", or "targeting microbubble" may be used synonymously.

"Targeted microbubble contrast enhanced ultrasonography" (targeted MCU) is a name given to such a technique whereby targeting microbubbles are introduced into a subject or system, and the microbubbles are imaged using an US device. Examples of a suitable device includes, but are not limited to, the Siemens Acuson Sequoia 512 ultrasound system (using, for example, its contrast pulse sequencing (CPS) imaging mode), Phillips HDI5000 ultrasound system (using, for example, pulse inversion imaging mode), Phillips Sonos 5500 ultrasound system (using, for example, power modulation imaging mode), or VisualSonics Vevo 770 (using for example linear imaging mode) or Vevo 2100 (using, for example, non-linear imaging mode).

A short period of time after microbubble administration, part of the microbubble population will have adhered to the molecules of interest, and are described as retained microbubbles, while others may remain free, described as free microbubbles. Retained microbubbles are microbubbles retained or accumulated in a tissue or system (for example a flow chamber system) due to adherence to the molecule(s) of interest. Retained microbubbles may also be retained in a tissue or system due to other mechanisms including, but not limited to, non-specific adherence or cellular-uptake. Free microbubbles are microbubbles that circulate freely in a tissue or system. Both retained and free microbubbles decrease in number over time owing to their elimination.

Targeted MCU has been used to determine the concentration of a molecule of interest (a target molecule), by measuring the retained microbubble signal intensity after a certain time following the introduction of the microbubbles such that the free microbubbles in the body or system have decreased through elimination to a relatively low level (for example when the signal caused by free microbubbles has become low, insignificant, minimal or undetectable). However, I have found this method of imaging signal analysis lacks sensitivity and has a low degree of quantification, as evidenced by it being poor at detecting low concentrations as well as small changes in the target molecule concentration. Furthermore, it is prone to inaccuracies, inconsistencies and wide variations. Alternative imaging signal analysis methods suffer from attenuation and/or saturation of microbubble ultrasound signals when microbubbles are at high or moderate concentrations, making signal analysis for the determination of the target molecule concentration very difficult or inaccurate. While these problems can be mitigated to some degree by reducing the number of microbubbles administered into the body or system so that signal attenuation and/or saturation either does not occur or is minimised, I have found that this reduces the number of target molecules that can be detected as well as the accuracy and degree of quantification of the target molecule concentration.

The foregoing identifies a major obstacle limiting the development of targeted MCU towards human application.

SUMMARY OF INVENTION

Accordingly, it is an aim to attempt to provide a method of imaging signal analysis which is robust and highly quantitative, and thus suitable for use in contrast imaging (molecular imaging) of human subjects as well as animals, in particular for targeted MCU. The method may have one or more advantages, including but not limited to: higher sensitivity, accuracy and degree of quantification for the molecular targets; more robust and reproducible, higher dose of contrast agents (e.g., targeting microbubbles in targeted MCU) can be used, which can be administered as a bolus (continuous infusion may also be used); other useful physical properties can be obtained simultaneously, such as the retained or free contrast agent half-life; tissue fractional vascular volume may also be obtained. For example, the method may quantify a wider range of target molecule concentrations as well as detecting smaller changes in them.

According to an aspect of the invention there is provided a method of quantifying the characteristics of an object using imaging, the object treated with a contrast agent, comprising: receiving, from an imaging system, a plurality of imaging signals of the object captured over a period of time; measuring, at a data processing system, the signal intensity in each of the plurality of imaging signals corresponding to a point on the object; and curve fitting, at the data processing system, the measured signal intensity of the point on the object to a bi-exponential function comprising a first and a second exponential term, the first exponential term representing the decrease in concentration of the contrast agent which is free over time and the second exponential term representing a decrease in concentration of the contrast agent which is retained on the object over time.

According to another aspect of the invention there is provided a system for quantifying the characteristics of an object using imaging, the object treated with a contrast agent, comprising a data processing system arranged to: receive a plurality of imaging signals of the object captured over a period of time; measure the signal intensity in each of the imaging signals corresponding to a point on the object; and curve fit the measured signal intensities of the point on the object to a bi-exponential function comprising a first and a second exponential term, the first exponential term representing the decrease in concentration of the contrast agent which is free over time and the second exponential term representing a decrease in concentration of the contrast agent which is retained on the object over time. The system may further comprise an imaging system arranged to capture the plurality of imaging signals of the object over the period of time.

According to yet another aspect of the invention there is provided apparatus for quantifying the characteristics of an object using imaging, the object treated with a contrast agent, wherein the apparatus comprises a data processing system configured to carry out any suitable method disclosed herein.

According to another aspect of the invention a computer program is provided comprising computer readable code which is operable in use to instruct a computer to perform any method of quantifying the characteristics of an object using imaging disclosed herein.

According to a further aspect of the invention a computer-readable medium is provided which comprises computer readable code which is operable in use to instruct a computer to perform any method of quantifying the characteristics of an object using imaging disclosed herein.

According to yet a further aspect of the invention a non-transitory computer readable medium is provided comprising computer program code which is operable in use to instruct a computer to perform any method of quantifying the characteristics of an object using imaging disclosed herein.

In one aspect of the invention, there is provided a method of quantifying the characteristics of an object using imaging, the object treated with a contrast agent, which comprises:
(a) capturing a plurality of imaging signals of the object over a period of time;
(b) measuring the signal intensity in each of the plurality of imaging signals corresponding to a point on the object; and
(c) curve fitting the measured signal intensity of the point on the object to a bi-exponential function comprising first and second exponential terms, the first exponential term representing the decrease in concentration of the contrast agent which is retained on the object over time and the second exponential term representing a decrease in concentration of the contrast agent which is free over time.

The measured signal intensities curve fitted may be those after the concentration of the contrast agent is less than the point where saturation and/or attenuation of the signal intensity is significant.

The imaging signals analysed can be from any suitable imaging modality as described. In one arrangement, imaging signals from US imaging (e.g., targeted MCU) are analysed.

Suitable imaging signals captured in step (a) can be any suitable imaging signal as described. In one arrangement, (a plurality of) images are captured as the (plurality of) imaging signals.

Suitable signal intensity measured in step (b) can be any suitable signal intensity as described. In one arrangement, image pixel intensity (videodensity) is measured as the signal intensity.

The signal intensity at a point or region of interest may be corrected for background signal and/or noise before carrying out step (c). This may be done, for example, by subtraction using pre-contrast administration imaging signal intensity at the same point or region of interest of the object.

In a second aspect of the invention, a method that runs in the central processing unit (CPU) of a computer or imaging device, to analyse and transform imaging signals (electrical signals) to represent the concentration and elimination characteristics of contrast agents as disclosed, more specifically it identifies the concentration and elimination characteristics of the retained contrast agent from that of the free contrast agent, allowing useful results to be obtained which include, but are not limited to, the concentration/expression level of a target molecule in a tissue imaged, the tissue fractional vascular volume, the half-life of retained or free contrast agent in a tissue/object/subject—these can be applied, for example, in clinical decision making (e.g., the concentration/expression level of a molecule of interest can be used in diagnosis, prognosis, and/or assessing disease progression/resolution), or in assessing pharmacokinetic profile of contrast agents (e.g., the contrast agent half-life can be used in assessing correct/safe dosing of the contrast agent).

As mentioned, embodiments of the invention have a number of advantages, including a higher degree of quantification of molecular targets. As different types, severity and stages of disease may express different combinations of molecules and in different concentrations, embodiments of the present invention provide a more robust method which increases the degree of quantification of molecular imaging, such as in US molecular imaging.

The plurality of imaging signals may be captured once the concentration of contrast agent is less than the point where attenuation and/or saturation of the signal intensity is significant.

The bi-exponential function may comprise:

$$I(t) = A_f e^{-\lambda_f t} + A_r e^{-\lambda_r t}$$

where I is the detected signal intensity representing the concentration of contrast agent, $A_f$ represents the maximum concentration of free contrast agent in the elimination phase, $A_r$ represents the maximum concentration of retained contrast agent in the elimination phase, $\lambda_r$ is the elimination rate constant for retained contrast agent, $\lambda_f$ is the elimination rate constant for free contrast agent, and t is the time after termination of contrast agent administration.

The contrast agent may be a plurality of microbubbles, but other types of contrast agents are also suitable. The processing of the imaging signals allows larger numbers of microbubbles to be used without imaging signal saturation and/or attenuation causing the problems set out above. The bi-exponential function allows separation of the retained microbubble signal from that of the freely circulating ones. Images can be processed after the event, meaning that post processing can be used remotely.

A plurality of ultrasound images may be captured in step (a) once the concentration of microbubbles is less than the point where saturation and/or attenuation of the signal intensity occurs or becomes significant.

At least one of the following characteristics can be quantified: the concentration of free contrast agent in the elimination phase ($A_f e^{-\lambda_f t}$) and its maximum ($A_f$), the concentration of retained contrast agent in the elimination phase ($A_r e^{-\lambda_r t}$) and its maximum ($A_r$), area under the curve (AUC) for free contrast agent $$\left( AUC_f = \frac{A_f}{\lambda_f} \right)$$

or retained contrast agent $$\left( AUC_r = \frac{A_r}{\lambda_r} \right)$$

in the elimination phase, the elimination rate constant of retained contrast agent ($\lambda_r$) or free contrast agent ($\lambda_f$), and the half-life of retained contrast agent $$\left( \frac{Ln2}{\lambda_r} \right)$$

or free contrast agent $$\left( \frac{Ln2}{\lambda_f} \right).$$

The fractional vascular volume of a tissue may also be obtained by taking the ratio of the maximum concentration ($A_f$) or area under the curve ($AUC_f$) of free contrast agent from two regions of interest, the denominator being that for the region of interest placed in a blood pool region such as in a nearby blood vessel or heart cavity.

According to one arrangement, the method further may comprise the steps:
(d) repeating steps (b) & (c) for points across a region of interest of the object; and
(e) averaging the quantified characteristic.

According to another arrangement, the method may further comprise the steps:
(d) repeating step (b) for points across a region of interest of the object;
(e) averaging the signal intensities of points across the region of interest at particular times; and
(f) carrying step (c) out on the average signal intensities.

A videodensitometric method may be used to process the images, for example, images from US, MRI, or PET contrast imaging.

According to one arrangement, the method may further comprise the steps of:
(d) repeating steps (b) & (c) for points across at least a part of the object; and
(e) creating an image of the concentration of the contrast agent on the object based on the quantified characteristics of the points on the object.

According to one arrangement, the method may further comprise the steps:
(d) repeating steps (b) and (c) for points across at least a part of the object; and
(e) creating an image comprising the quantified characteristic for at least part of the object.

According to one arrangement, the biexponential equation may further comprise an additional component(s), such as (but not limited to) a constant(s), a scaling factor(s), a factor(s) or an exponential term(s). This may be used to account for factors such as (but not limited to) background signal, system noise, or cellular internalisation of the contrast agent. For example, an additional exponential term may be used in the latter; while a constant may be used for one or both of the former two. Thus, the bi-exponential function may comprise a constant (K), e.g., $$I(t)=A_f'e^{-\lambda_f t}+A_r'e^{-\lambda_r t}+K$$

One may obtain $A_r$ and $A_f$ using, $A_r=A_r'-K[A_r'/(A_f'+A_r')]$ and $A_f=A_f'-K[A_f'/(A_f'+A_r')]$, respectively.

In one arrangement, a plurality of images (as the imaging signals) from targeted MCU may be captured in step (a), and image pixel intensity (as the signal intensity) is measured in step (b).

Contrast agents may be administered as a bolus or infusion. One aspect of the invention may allow high contrast dose (to allow saturation of contrast-to-target molecule binding for accurate/reproducible quantification of target molecule expression level/concentration) causing signal saturation and/or attenuation to be used. For bolus administration, this may be given over upto a few seconds. For administration as an infusion, the contrast agent may be administered as a continuous infusion over a sufficient period of time (eg several minutes) to allow saturation of contrast agent-to-target molecule binding or contrast agent retention. The infusion is then stopped. Contrast agent signal intensities will then start to decrease, a plurality of imaging signals may then be captures and processed in the same way as described.

BRIEF DESCRIPTION OF THE DRAWINGS

The present invention will now be described by way of example only with reference to the drawings in which:

FIG. 4A Esel mRNA. Each data point represents one animal. Exponential line of best fit ±95% confidence interval (CI) is shown. FIG. 4B Esel cell-surface protein. Each data point represents mean±95% CI for 5, 5, 4, 5 mice at $LPS_{Time}$ 3, 5, 8, 24 h, respectively. Exponential line of best fit ±95% CI is shown. FIG. 4C Esel mRNA vs Esel cell-surface protein;

FIG. 5A Sequential 14 MHz Contrast Pulse Sequencing (CPS) images of the heart in end-diastole parasternal short-axis (PSA) view, in a (1) wild-type (WT) and (2) Esel knock-out (KO) mouse pre-treated with LPS, respectively. TICs of the left ventricular (LV) cavity (from region of interest (ROI) C) and myocardium (from ROI M) for the respective animal are shown beneath; each data point represents background subtracted mean signal intensity (I)±SD; suggested bolus (B), distribution (D) and elimination-phase (E) of the time signal intensity curve (TIC) are indicated. FIG. 5B PSA, parasternal long-axis (PLA) and apical 4-chamber (A4C) views of the heart at 14 and 7 MHz CPS, >20 min post bubble administration (when freely circulating-bubbles have cleared from the blood pool (LV cavity). Animal, gain and mechanical index (MI) were the same between both frequencies. Arrow indicates mid anteroseptal wall. Baseline images before bubble administration are shown in FIG. 6;

FIG. 7A WT=−0.78, KO=−0.05; FIG. 7B WT=−0.87, KO=−0.08; FIG. 7C WT=0.79, KO=0.43; FIG. 7D WT=0.81, KO=not applicable; FIG. 7E WT=0.84, KO=not applicable; FIG. 7F WT=0.67, KO=0.16. In FIG. 7G: $R^2$=0.77 (exponential fit) or 0.87 (sigmoidal fit). Solid circle=WT, open circle=Esel KO. Error bar represents SD. †The group mean half-life of acoustically effective bubbles in vivo was calculated from $$\frac{Ln2}{\lambda}$$

of individual animals, and is not expected to be equal to $$\frac{Ln2}{\text{group mean } \lambda};$$

FIG. 8 is a table of example data; and

Figure 9:
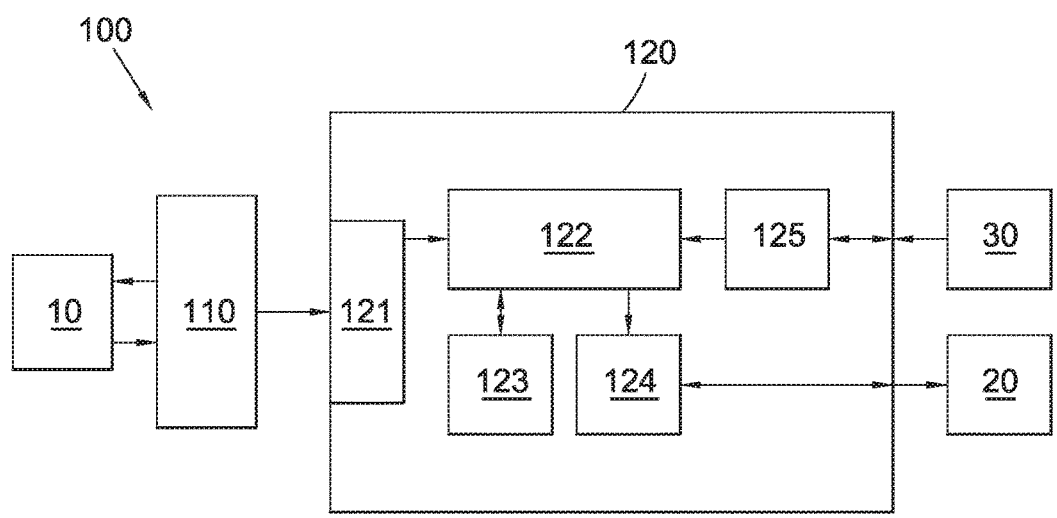

FIG. 9 illustrates a system used for implementing the method for quantifying the characteristics of an object using imaging as described herein.

SPECIFIC DESCRIPTION

The use of US scanners to image organs within a body non-invasively is well known. It is also known to enhance the images that are obtained by introducing targeting microbubbles intravenously (iv), the microbubbles being contrast agents which are visible to US imaging apparatus, the shell of the bubble being designed to adhere to molecules of interest (target molecules) in the tissue or organ to be imaged in a process called "targeted microbubble contrast enhanced ultrasonography" (targeted MCU).

In one embodiment of the present invention, targeting microbubbles are used as a contrast agent and US imaging is used for their detection. Targeting microbubbles are introduced into the body to adhere to target molecules, and images of a region of interest are collected spaced over a period of time. A point in the region of interest (ROI) can be selected, the pixel on each of the US images corresponding to that point can be identified, and the bubble US signal intensity of those pixels are measured and curve fitted to a bi-exponential function. The bi-exponential function comprises two exponential terms, one of which is related to the elimination of retained targeting microbubbles which have adhered to target molecules, and the other being related to the elimination of free targeting microbubbles which have not adhered and circulate freely. Once the curve has been identified, various characteristics of the targeting microbubbles and targeted molecules to which they attach can be identified.

This process is repeated for a number of other points in the region of interest from the same images in order to obtain the various characteristics for a number of points within the region of interest. The values of those various characteristics can then be averaged in order to obtain a very accurate quantification of the characteristics for that region of interest.

For example, one characteristic of importance might be the concentration of retained microbubbles because this quantifies the concentration or expression level of target molecules in the region of interest. The concentration of target molecules in the region of interest might be indicative, for example, of the presence or extent of a disease.

Another characteristic might be the half-life of the free and/or retained microbubbles. These can be determined in the same way, by identifying the curve to which the measured signal intensity of a point or region of interest shown in the images best fits.

In this way, important characteristics of a point or region of interest can be quantified. This can also be done for other points or regions of interest.

It might also be useful to create an image made up of a particular characteristic at each of the points of interest which have been quantified.

Figure 1:
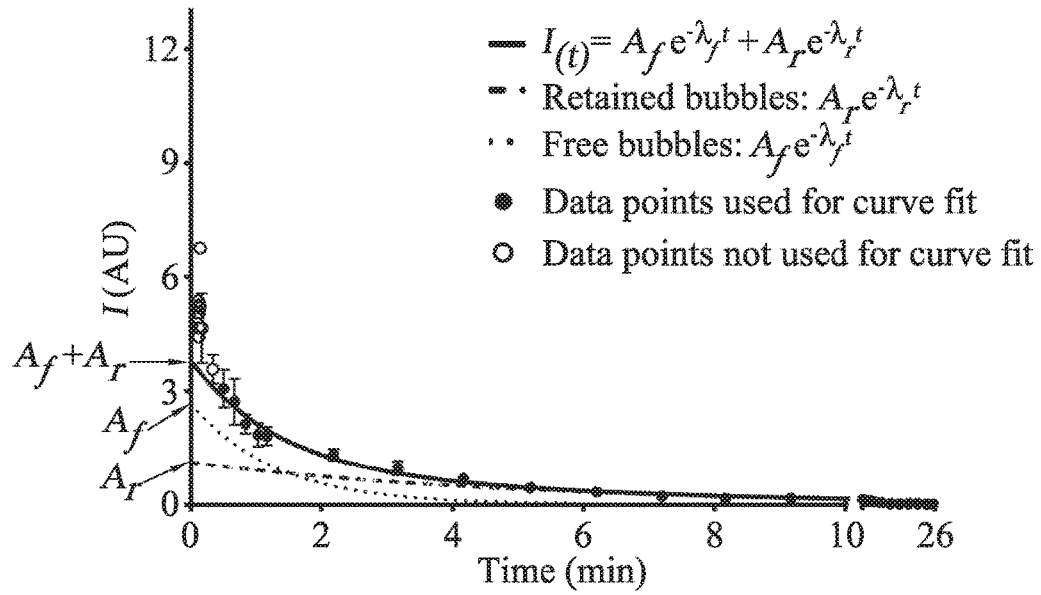
FIG. 1 is a graph showing ultrasonic (US) time-signal intensity curve for retained microbubbles, free microbubbles and for free and retained microbubbles.
Figure 2:
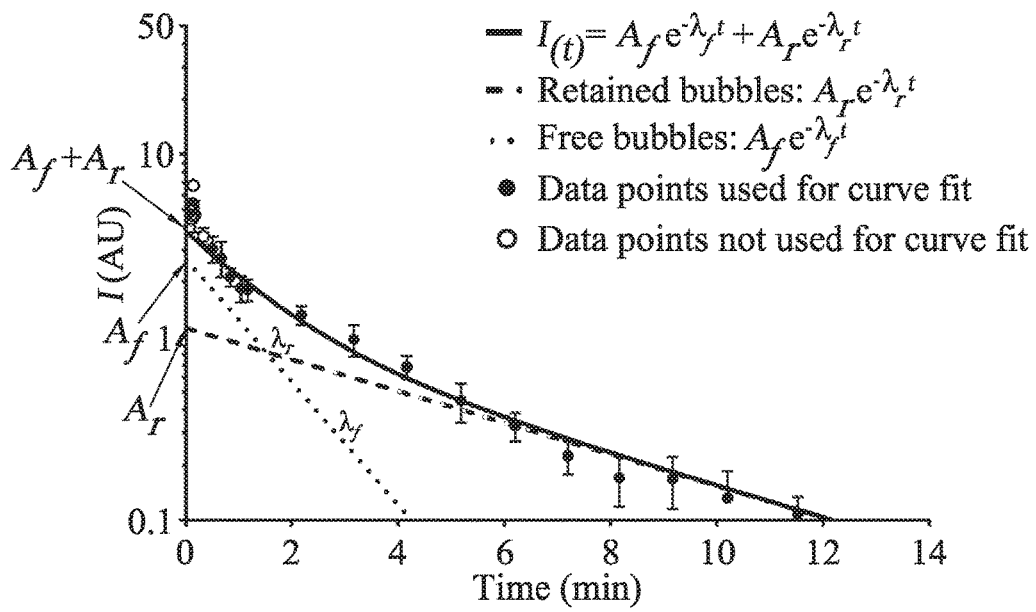
FIG. 2 is a graph showing, in semi-logarithmic form, the ultrasonic time-signal intensity curve for retained microbubbles, free microbubbles, and for the combined free and retained microbubbles.

It is important to understand the significance of the bi-exponential curve mentioned above. A short time after the microbubbles are introduced into the body/system, a minor proportion of those microbubbles will attach themselves to target molecules, but many will remain unattached. The concentration of the free microbubbles decreases quite quickly. The concentration decreases through a number of different elimination mechanisms, including phagocytosis in the liver and spleen, deflation by gaseous diffusion in the bloodstream. This elimination is shown quite clearly in FIGS. 1 and 2. In FIG. 1, the elimination of the free microbubbles is faster than the elimination of the retained microbubbles. In FIG. 2, the elimination rate constant of free bubbles is a substantially straight line having a steeper gradient than that of retained bubbles.

The concentration of microbubbles in the elimination phase can be defined by the following bi-exponential function:

$$\text{Concentration of microbubbles}(t) = A_f e^{-\lambda_f t} + A_r e^{-\lambda_r t}$$

where $A_f$ is the maximum concentration of free microbubbles in the elimination phase, $A_r$ is the maximum concentration of retained microbubbles in the elimination phase, $\lambda_f$ is the elimination rate constant of free microbubbles, and $\lambda_r$ is the elimination rate constant of retained microbubbles.

Of course, you would expect the detected concentration in an US image for a particular point to correspond to the actual concentration of microbubbles. As described above, the detected concentration of microbubbles becomes inaccurate (under-estimated) due to signal saturated and/or attenuated at high or moderate concentrations. However, for accurate and reproducible quantification of molecular targets, a relatively high dose of targeting microbubbles (to allow saturation of bubble-to-target molecule binding) is required. Signal intensities may be curve fitted after the point at which saturation and/or attenuation is low or no longer a factor. This means that one may wait for a few minutes after the microbubbles have been introduced into the body before imaging and using the signal intensity values for curve fitting. Looking, for example, at the curves shown in FIG. 1, imaging signals may be obtained from US imaging after about 2 to 6 min post bolus administration of the microbubbles into the body. Curve fitting the signal intensities after this point has the effect that the exponential function for the retained microbubbles are extrapolated back to the initial (maximum) concentration $A_r$. This also applies for the free microbubbles. In this way, the disadvantages of the prior art are overcome.

Below is an example of how one embodiment of this invention is applied in quantifying the characteristics of the heart of a mouse treated with a contrast agent. This method can, of course, be applied to quantifying the characteristics of other tissues or organs of a mouse, or indeed, the tissues or organs of other animals, including humans.

Example

In this example, an inflammatory response was stimulated to cause the heart to express E-selection (Esel) to which the microbubbles adhere. Wild type (WT) mice were first injected with lipopolysaccharide (LPS) to induce systemic inflammation. The heart's inflammatory response was to express Esel (an endothelial adhesion molecule expressed on activated endothelium during inflammation). Microbubbles were introduced into the cardiovascular system which adhered to Esel molecules (target molecules), and the accumulation of bubbles attached to Esel targets in the heart allowed the heart to be quantitatively analysed (e.g., for Esel concentration or expression level indicative of the degree of endothelial activation or inflammation) from ultrasound (US) images, using one aspect of the invention.

Experimental Details

Antibodies

MES-1 monoclonal antibody (mAb), a rat IgG2a,k against mouse Esel, and its F(ab')$_2$ fragment (MES-1 F(ab')$_2$) was provided by Dr D Brown (UCB Celltech, UK). Reduced MES-1 F(ab')$_2$, containing 2 thiol groups per F(ab')$_2$, were prepared by tris(2-carboxyethyl)phosphine hydrochloride (TCEP) reduction. MEC13.3 mAb, rat IgG2a,k against mouse PECAM-1 (BD Biosciences). Rat IgG2a,k isotype negative control mAb (BD Biosciences). Biotinylated rabbit mAb against rat IgG2a (secondary antibody) (Vector Laboratories).

Esel Targeting Microbubble Preparation

Maleimide-functionalised lipid-shelled octafluoropropane ($C_3F_8$) microbubbles were prepared by sonication of a gas-saturated aqueous suspension of 1,2-distearoyl-sn-glycero-3-phosphocholine (DSPC; Avanti Polar Lipids, AL), 1,2-distearoyl-sn-glycero-3-phosphoethanolamine-N-(maleimide(polyethylene glycol)-2000) (DSPE-PEG2000-Mal; Avanti Polar Lipids), mono-stearate poly(ethylene)glycol (PEG40 stearate; Sigma-Aldrich), and fluorescent dye 1,1'-dioctadecyl-3,3,3',3'-tetramethylindocarbocyanine perchlorate (DiI; Molecular Probes) at 75:9:14:2 molar ratio, in the presence of $C_3F_8$. Approximately $4.338 \times 10^6$ TCEP reduced MES-1 F(ab')$_2$ molecules per bubble were incubated for 30 min at 4° C., near neutral pH, under $C_3F_8$ atmosphere with constant gentle agitation; the reaction was terminated by adding excess N-Ethylmaleimide (Sigma-Aldrich) to quench any unreacted thiol. Microbubbles were washed with cold degassed normal saline using multiple cycles of centrifugation flotation under $C_3F_8$ atmosphere at 4° C. before and after microbubble conjugation, to remove unincorporated components and particle fragments. Freshly prepared Esel targeting microbubbles were immediately divided into 20-50 μl aliquots, capped and sealed with parafilm (American National Can), then snap frozen in liquid nitrogen and stored at −80° C. until use. The concentration and size of subsequently thawed Esel targeting microbubbles were, respectively, $1-3 \times 10^9$ bubbles/ml and diameter 2.2(mean) ±0.2(SEM) μm (98.6% or 100% of the bubbles were under 6 or 10 μm in diameter, respectively). The Esel targeting microbubbles were sufficiently echogenic, stable, lacked non-specific binding, and produced no immediate adverse effects in vivo.

Animals

Wild-type (WT) mice: adult male C57B16/Jax (Charles River, UK). Esel knock-out (KO) mice: adult male Esel homozygote KO on C57B16 background, bred locally from mice donated by Dr K Norman and Prof P Hellewell (University of Sheffield, UK). All the animal work was carried out under Project Licences and Personal Licences granted by the Home Office under the Animals (Scientific Procedures) Act 1986; ethical approval was additionally obtained from the local Ethical Review Panel.

Lipopolysaccharide (LPS) Mouse Model (Experimental Endotoxaemia)

WT and Esel KO mice were pre-treated with 50 µg LPS from E Coli 0111:B4 (Sigma-Aldrich), made up to 200 µl volume in normal saline, by intraperitoneal (ip) injection to induce systemic inflammation. Systemic administration of LPS by ip injection produces systemic inflammation, which includes induction of Esel expression in multiple organs including the heart and kidneys.

Immunohistochemistry

Immunohistochemistry was performed on acetone-fixed cryosections of freshly harvested hearts of WT (with/without LPS pre-treatment) and Esel KO (pre-treated with LPS) mice. After blocking non-specific binding sites with 100 µl of 1:1000 rabbit serum (Sigma-Aldrich) for 1 hour (h) at room temperature (rt), sections were incubated for 1 h at rt with 100 µl of 0.01 mg/ml primary antibody: MES-1 (for Esel), MEC13.3 (for PECAM-1, endothelial marker) or isotype negative control. Each section was then incubated with 100 µl of 0.005 mg/ml biotinylated secondary antibody for 60 min at rt. After blocking of endogenous peroxidase with 0.3% $H_2O_2$ methanol for 20-30 min at rt, the horseradish peroxidase-based detection system, Vectastain ABC kit (Vector Laboratories), was used with 3,3'-Diaminobenzidine solution (SIGMAFAST™ DAB tablet, Sigma-Aldrich) as the chromogen substrate. Sections were counterstained using Harris Modified Hematoxylin Solution (Sigma-Aldrich) and 1% $NaHCO_3$, then dehydrated through 70-100% ethanol, dried and mounted with Histomount (VWR), and examined under light microscopy. The duration between the time of LPS pre-treatment and sacrifice of the animal for immediate tissue harvesting was noted as the $LPS_{Time}$.

Reverse Transcriptase—Real Time Quantitative Polymerase Chain Reaction (RT-qPCR).

WT mice were pre-treated with LPS as described above. The duration between the time of LPS pre-treatment and sacrifice of the animal for immediate tissue harvesting was noted as the $LPS_{Time}$. Freshly harvested tissues were kept in RNAlater® solution (Ambion) to preserve ribonucleic acid (RNA) in-situ; total RNA was subsequently extracted using TRIzol reagent (Invitrogen) according to the manufacturer's instructions. First-strand complementary deoxyribonucleic acid (cDNA) synthesis was then performed using the Qiagen Omniscript® Reverse Transcription kit (Qiagen) according to the manufacturer's instructions. This was followed by real-time qPCR with the SYBR®Green detection method for Esel and hypoxanthine phosphoribosyltransferase-I (HPRT-I), carried out on a 96-well plate in the iCycler™ (iCycler iQ Real-Time PCR Detection System, Bio-Rad) according to the manufacturer's instructions. All PCR reactions were carried out in triplicate wells on the same plate. The primer sequences were: Esel forward primer 5'-CTCAT-TGCTCTACTTGTTGATG-3', Esel reverse primer 5'-GCATTTGTGTTCCTGATTG-3', HPRT-I forward primer 5'-ATTAGCGATGATGAACCAG-3', HPRT-I reverse primer 5'-AGTCTTTCAGTCCTGTCCAT-3'. For data analysis, the threshold cycle (Ct) was determined from the amplification plot using the iCycler™ iQ Optical System Software Version 3.0a (Bio-Rad). As PCR efficiency of the Esel and HPRT-I primer pairs differed by ≤5% (93±4% and 92±3% (mean±SD), respectively; n=4 each), comparative Ct method was used to estimate the amount of Esel messenger (mRNA) relative to that of HPRT-I, using the formula: Esel mRNA (% HPRT–I)=$2^{-\Delta ct}$, where $\Delta Ct = Ct_{Esel} - Ct_{HPRT-I}$ subscripts refer to the gene of interest. Mean of the replicates was used and plotted against $LPS_{Time}$ for each animal.

Further details of the methodology is as follows. The yield of total RNA from the mouse heart was typically ≈1 µg pure RNA per 1 mg tissue, kept at concentrations over ≈1 mg/ml in molecular grade (RNase-free) $H_2O$ (Sigma-Aldrich). The RT reaction mixture for first-strand cDNA synthesis consisted of 1 µg total RNA, 2 µl 10× buffer RT, 2 µl deoxyribonucleotide triphosphate (dNTP) mix (5 mM each 2'-deoxyadenosine 5'-triphosphate (dATP), 2'-deoxycytidine 5'-triphosphate (dCTP), 2'-deoxyguanosine 5'-triphosphate (dGTP), 2'-deoxythymidine 5'-triphosphate (dTTP), 1µ (4 units) Omniscript reverse transcriptase, 2 µl (1 µg) oligo $(dT)_{12-18}$ primer (Invitrogen) and molecular grade $H_2O$ made up to a total reaction volume of 20 µl, incubated for 1 h at 37° C. qPCR was carried out in a 25 µl-reaction volume in each well of a 96-well 0.2 ml thin-wall PCR plate (Bio-Rad) covered with an Optical Quality Sealing Tape (Bio-Rad). The qPCR reaction mixture consisted of 5 µl cDNA template (1:50 water dilution of the finished RT reaction), 0.5 µl (10 µM) each of the forward and reverse primer for the respective gene (see text for primer sequence; the primers were custom ordered from Invitrogen), 6.5 µl molecular grade $H_2O$ and 12.5 µl iQ™ SYBR® Green Supermix (Bio-Rad). The qPCR cycling condition was: initial 3 min denaturing step at 95° C. (Well Factor analysis in first 90 s); then 40 cycles of 15 s at 95° C., 1 min at 56° C.; melt-curve analysis in 0.5° C. steps (1 min denaturation at 95° C., 1 min reset at 56° C., then 80 cycles of 10 s at 60° C. with 0.5° C. increment for each cycle); final cooling step at 4° C. Esel and HPRT-I were amplified on the same plate for each animal; no-template negative control using molecular grade $H_2O$ in place of cDNA template for both primer pairs were included in all plates. For data analysis, wells with abnormal amplification plot or melt-curve were excluded.

Ultrasound (US) Imaging

WT and Esel KO mice were all pre-treated with LPS, tail vein cannulated and anaesthetised with xylazine/ketamine mixture as described above. The chest, abdomen and pelvis were then shaved and the animal placed supine. ECG electrode pads (Ambu® Blue Sensor P, Ambu) were applied to the paws and connected to the US machine (Acuson Sequoia® 512 US system, Siemens, CA) equipped with 'Small Animal ECG Filter'. A layer of warm gel (Gel for ultrasonic & electrical transmission, Henleys Medical) was coupled between the skin and US transducer (15L8-s linear array transducer, foot print 26 mm, Siemens). US settings used were: 14 MHz (P14 MHz, spatial resolution ≈0.2 mm) Contrast Pulse Sequencing (CPS) mode (a non-linear imaging mode specific for microbubbles), transmission power 9 dB giving low mechanical index (MI) 0.22-0.26 estimated by the scanner, dynamic range 55 dB, time gain 0%, CPS gain 8, fundamental 2D gain 15 dB, colour map M:3 (bubble signal presented in heated object scale (CPS-contrast only' images), tissue signal in grey scale (B-mode' images)), TEQ was not used. Before bubble injection, baseline parasternal short axis (PSA) view at the papillary muscle level, parasternal long axis (PLA) and apical 4-chamber (A4C) views of the heart with and without 'regional expansion selection' (RES; giving magnified images with enhanced resolution) were recorded as 3 s-digital clips. Thereafter, imaging was maintained in the PSA view with the transducer fixed in position using a free standing clamp. A stopwatch was then started and a high dose of $1\times10^8$ Esel targeting bubbles (in 100 µl volume made up with normal saline) injected at 10 s via the tail vein catheter as a rapid iv bolus over 1-2 s, followed by a 100 µl-normal saline flush over 1-2 s at 20 s. Continuous US insonation was applied without pausing from time 0-1 min 23 s on the stop-watch, then paused, then resumed only for 3 s each time for digital image acquisition. 3 s-digital clips (RES activated) of the heart containing several consecutive cardiac cycles were recorded at 10 s and 13 s, then at 10 s intervals from 20 s-1 min 20 s, then at 1 min intervals from 2 min 20 s-10 min 20 s, then at 2 min intervals from 12 min 20 s-30 min 20 s, then at 5 min intervals until 60 min 20 s on the stopwatch (image acquisition was stopped earlier if particle contrast enhancement in the left ventricular (LV) cavity (central blood pool) was no longer visible). Unmagnified (non-RES) images of the thorax containing the heart in the PSA view and surrounding tissues were recorded at 5 min intervals. Other views of the heart (PLA and A4C views) were acquired at the end. In some animals, 7 MHz (P7 MHz, spatial resolution CPS imaging at MI 0.22 (gain and other settings kept the same as 14 MHz imaging) was also acquired at baseline and the end of the 14 MHz imaging study. When switching from 14 MHz to 7 MHz CPS imaging, the transmit power was first reduced from −9 dB to −19 dB before reducing the US frequency, to avoid an increase in MI (up to ≈0.7) causing inadvertent particle destruction. All animals received only one dose of bubbles to avoid carry-over effect from previous bubble dosing (e.g., blocking of Esel binding sites by previously administered Esel targeting bubbles). At the end of imaging, animals were sacrificed and tissues immediately harvested for frozen section immunohistochemistry and qRT-PCR as described above.

Time-Signal Intensity Curve (TIC) Generation

Figure 5A:
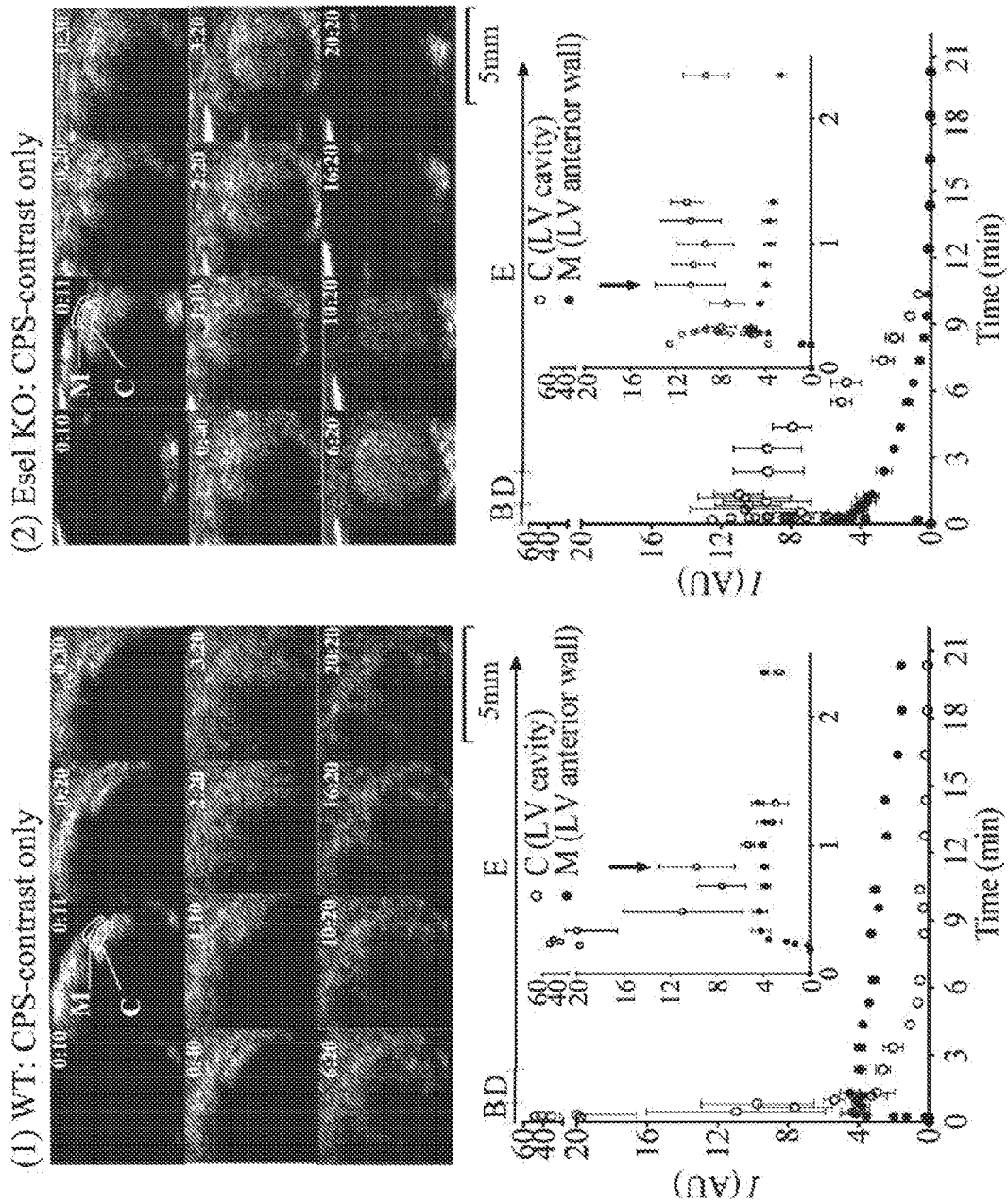
FIGS. 5A and 5B are graphs and images of real-time US molecular imaging of Esel expression in the mouse heart.

Videodensitometric method was used to measure particle signal intensity off-line, using the YABCO© software (LLC Charlottesville, Va.). End-diastolic image frames of the heart in the PSA view (CPS-contrast only' images) were selected and aligned, those that could not be aligned (e.g., due to large movement artefact) were excluded. Regions of interest (ROIs) were placed on the mid-anterior wall of the myocardium (M) and adjacent region in the LV cavity (C), as shown in FIG. 5A. These regions were chosen because they were consistently least or minimally affected by US attenuation in all animals. The video signal intensities (VI) were 'linearised' by log-decompression using the formula:

$$\text{Linearised } VI = 255 \times 10^{\left(\frac{VI-255}{255} \times \frac{dB}{20}\right)}$$

where dB is the dynamic range (55 dB in this study). Linearised VI (I) was expressed in arbitrary acoustic units (AU). I of several end-diastolic image frames within the 3 s-recording period at each time point were averaged, then corrected for background noise by subtracting away average I of the baseline images (images before particle administration) in the respective animals. TICs of the myocardium (tissue) and LV cavity (central blood pool) were constructed by plotting background-subtracted I of the myocardium and LV cavity, respectively, against time post bubble administration.

Quantitative Analysis of US Imaging (1) Bi-Exponential Curve Fit Method. The bi-exponential equation, $I(t)=A_f e^{-\lambda_f t}+A_r e^{-\lambda_r t}$, was curve fitted to the elimination-phase of the TIC of the myocardium, by iterative non-linear regression least squares method using the Prism 5.01 software (GraphPad Software, CA). The bi-exponential function was fitted using only consecutive data points at later time points, whose signal intensities lay within the linear acoustic range (when bubble concentrations have much reduced such that signal saturation and attenuation were minimal). In this study, the linear acoustic range was taken as I=0-5 AU, approximated from in vitro study of bubble concentration vs. signal intensity in a beaker using the same US settings as that for in vivo imaging. This resulted in fitting data points beyond ≈2-6 min post iv bubble bolus administration, which lay essentially in the elimination-phase of the TIC (FIG. 1), where Esel- or non-specifically-mediated bubble accumulation at target sites has essentially completed. Data points in the early part of the TIC with signal intensities I<5AU due to signal saturation and/or attenuation were not used for curve fitting. The resulting parameters of the curve fit $O_f$, $A_f$, $A_r$, $\lambda_r$ were analysed.

(2) A prior art method based on single late time point analysis was used for comparison with $A_r$ from present example of the invention. Baseline-subtracted bubble signal intensity in the myocardium at 20 min 10 s post bubble administration (R20), obtained as per TIC above, was used for analysis.

The $LPS_{Time}$ for US molecular imaging was taken as the duration between the time of LPS pre-treatment and administration of the targeting bubbles. The mean heart rate (HR) for each animal was calculated from all HRs recorded at different time points during cardiac imaging.

Statistics

Pearson correlation, linear or non-linear regression analysis was performed as indicated. Student's t-test or ANOVA with Turkey's post-hoc analysis was used for significance testing where indicated, with p<0.05 taken as significant.

Results

Esel Expression

Figure 3:
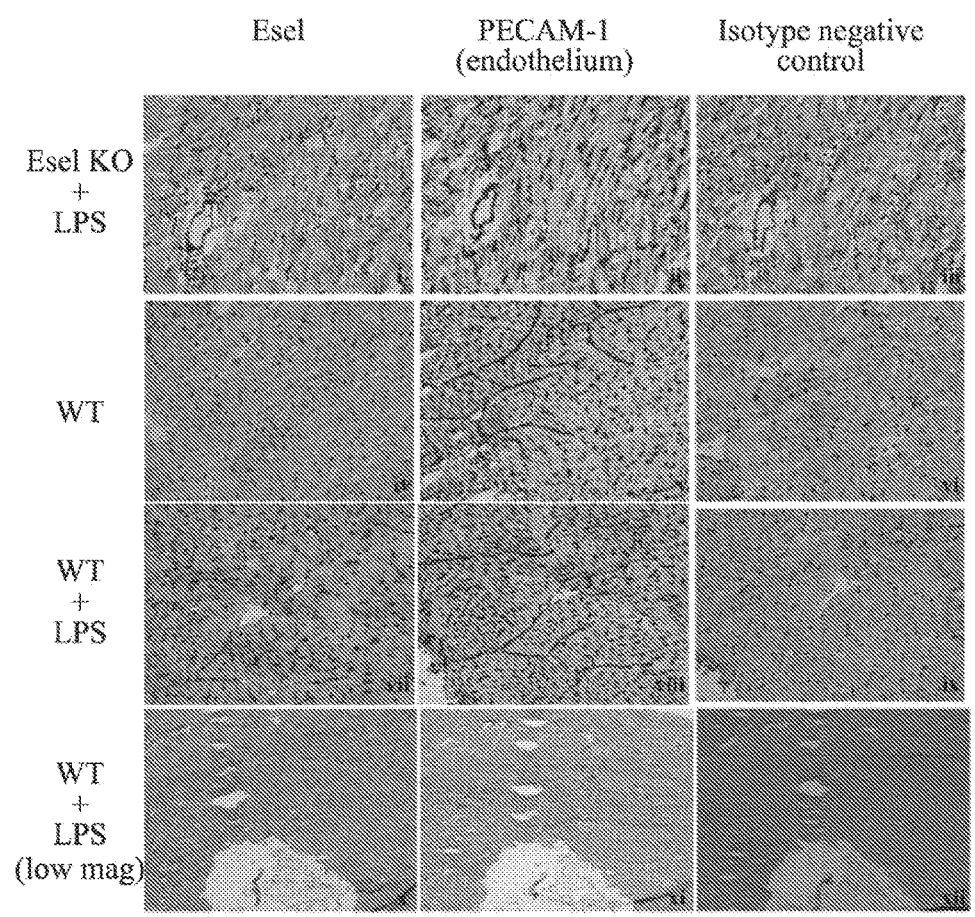
FIG. 3 shows a frozen section immunohistochemistry of the mouse heart. Representative example from mice 6h post lipopolysaccharide (LPS) pre-treatment. Magnification 200x. Low power magnification (low mag) 40x.

Frozen section immunohistochemistry showed that Esel was expressed in the heart of all WT mice pre-treated with LPS (n=35, $LPS_{Time}$=4-9 h). The spatial distribution was essentially uniform throughout the myocardium but limited to the post-capillary venules and capillaries. Esel was not detectable in the negative controls: WT mice not treated with LPS (n=5), and Esel KO mice pre-treated with LPS (n=10, $LPS_{Time}$=4-7 h), FIG. 3.

Quantification of Esel Expression by qRT-PCR.

Figure 4A:
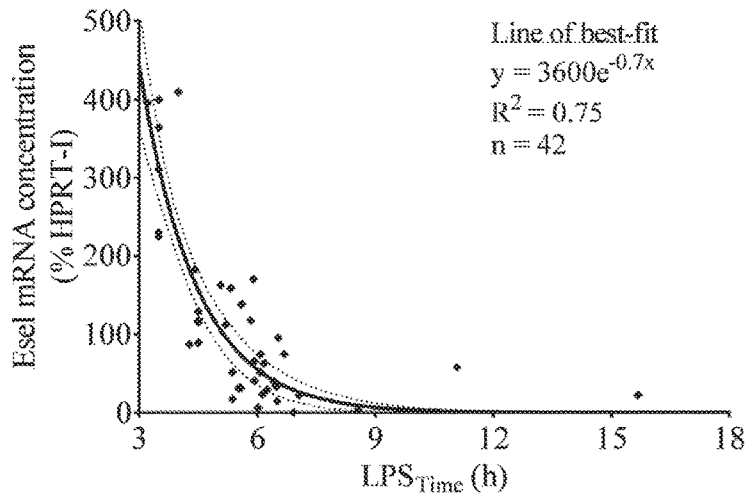
FIGS. 4A-4C are a series of graphs showing temporal expression of E-selectin (Esel) in the mouse heart.
Figure 4B:
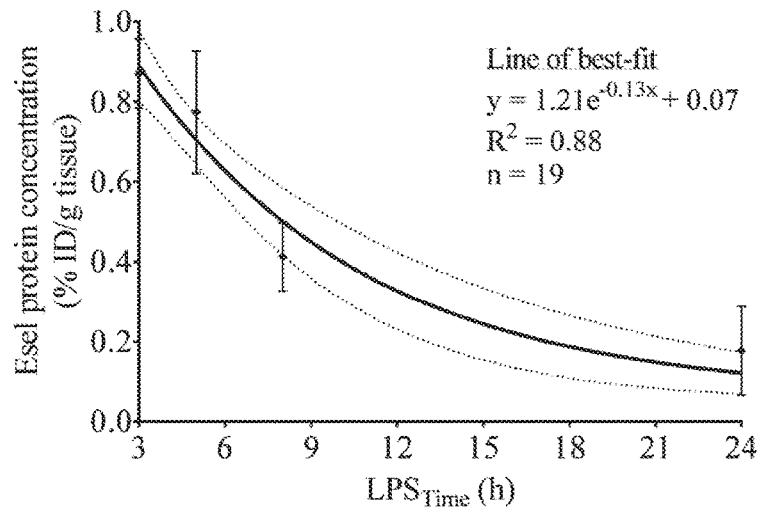

RT-qPCR showed that the concentration of Esel mRNA in the heart decreased exponentially with time after ≈3 h post LPS pre-treatment, reaching very low levels by ≈9 h (n=42, $LPS_{Time}$=3.2-15.7 h), FIG. 4B. This trend was similar to that of the cell-surface Esel protein concentration (expressed as % injected dose of radioactivity/g tissue (% ID/g tissue)) determined using iv radio-labelled mAb by Eppihimer et al[3] using the same strain, sex, and age of mice, as well as the same dose and route of LPS administration (n=19), FIG. 4B.

From the best-fit curves of Esel mRNA concentration vs. $LPS_{Time}$ mRNA (in % HPRT−I)=$3600e^{-0.7LPS_{Time}(in\ hours)}$, R=0.75) and that of Esel cell-surface protein concentration vs. $LPS_{Time}$ (protein (in % ID/g tissue)= $1.21e^{-0.7LPS_{Time}(in\ hours)}+0.07$, R2=0.88) using $LPS_{Time}$ as the common denominator, an empirical formula describing the relationship between the concentration of Esel mRNA and cell-surface protein could be derived as:

$$\text{Protein (in \% ID/g tissue)} = 1.21\left(\frac{mRNA \text{ (in \% HPRT} - 1)}{3600}\right)^{\frac{0.13}{0.7}} + 0.07,$$

Figure 4C:
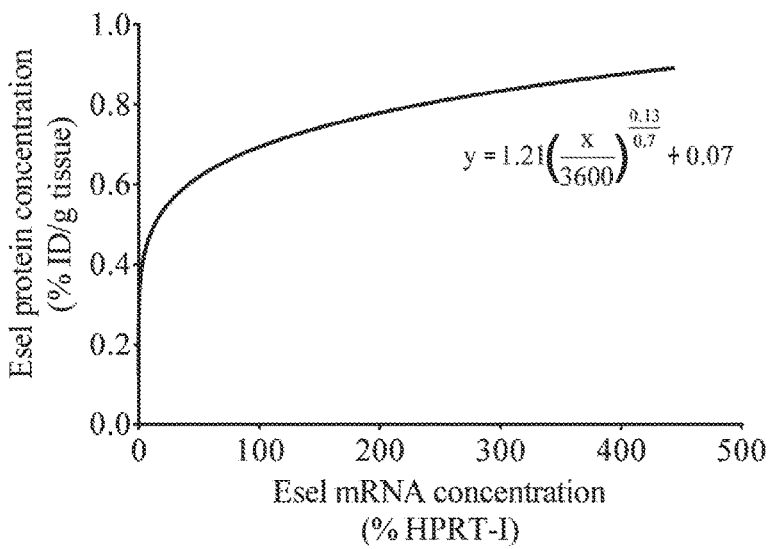

FIG. 4C. Thus the Esel cell-surface protein concentration was predictable from its mRNA concentration in the heart, in this LPS mouse model. Within the mRNA or protein concentration range (55-238% HPRT-I or 0.63-0.80% ID/g tissue, respectively) used for US quantification of Esel expression in this study, the relationship between the concentration of mRNA and cell-surface protein was approximately linear, allowing direct use of the mRNA concentration as a surrogate quantifier for the cell-surface protein concentration (the latter being the actual target of the targeting microbubbles).

Ultrasound Molecular Imaging
(1) Animals.

15 WT (age 5.7(mean)±0.2(SD) weeks, range 5.1-6.1 weeks; body weight 19.5(mean)±1.5(SD) g, range 17-22 g) and 8 Esel KO (age 7.9±3.2 weeks, range 5-13.6 weeks; body weight 22.3±3.7 g, range 17-28 g) mice were imaged. The duration between LPS injection and administration of targeting particles ($LPS_{Time}$) ranged 3:26-5:59 h for the WT and 4:27-5:39 h for the KO group.

(2) Cardiac Imaging.

Figure 5B:
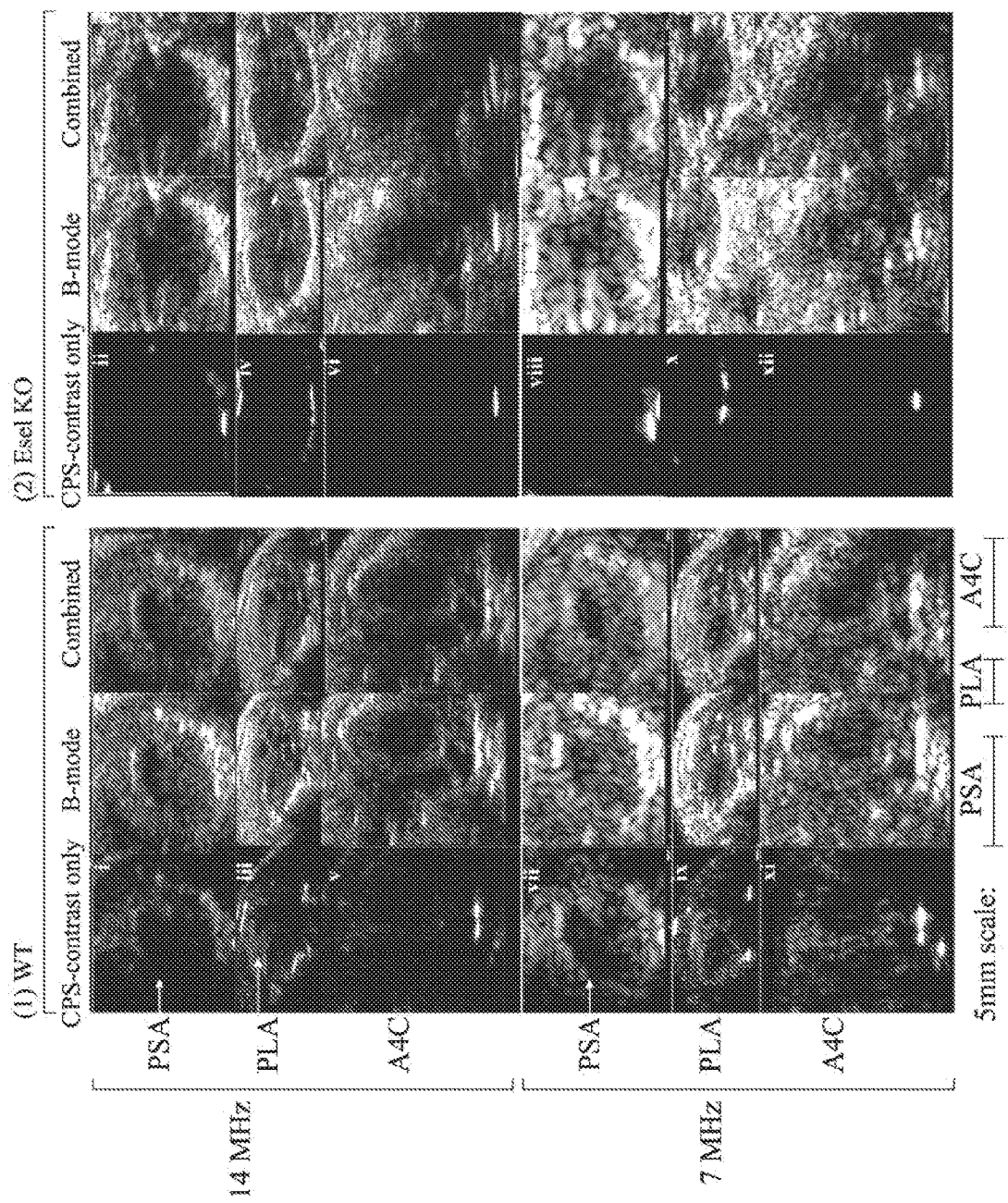
Figure 6:
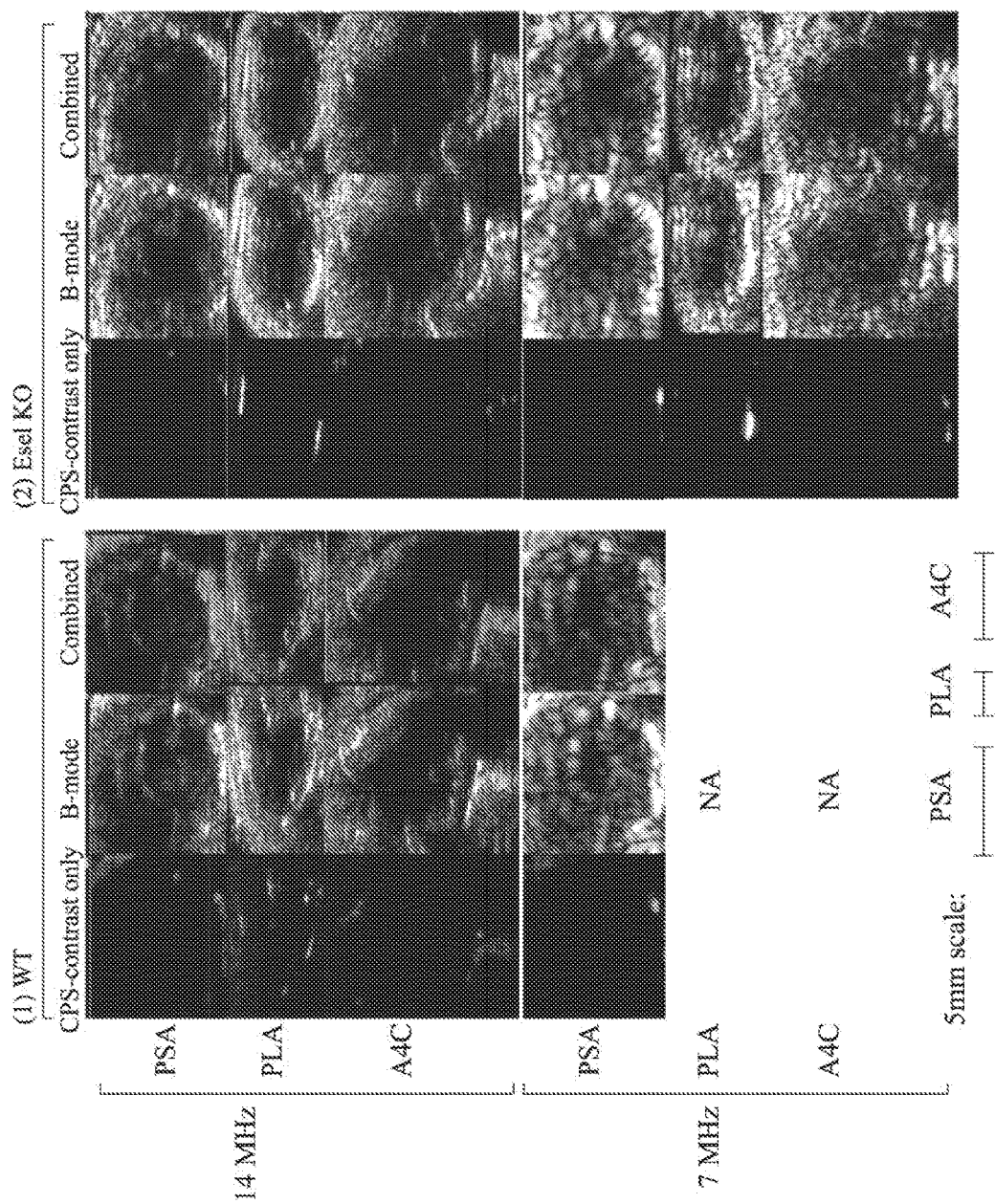
FIG. 6 includes a number of baseline images (before microbubble administration) for FIG. 5B.

Non-linear CPS artefacts (orange colour) present both before and after particle administration could be seen in WT and Esel KO animals; these artefacts were small and outside the myocardium, FIG. 5A (frame 0:10), FIG. 5A (2) (frame 20:20). Following iv bubble-bolus administration, bubble signal was first detected in the right heart chambers within 4 heart beats (≈1 s), the signal intensity rose rapidly. This was followed by the appearance of bubble signal in the left heart chambers as the bubbles returned from the pulmonary circulation. Bubble signal intensity in the LV cavity and myocardium peaked within 6-7 heart beats (≈1.5-2 s) and 9-12 heart beats (≈2-3 s) after bubble administration, respectively. Bubble signal intensity then decreased in the heart chambers and myocardium over time, FIG. 5A. Significant US attenuation due to high bubble concentration occurred early following bubble-bolus administration, with major loss of signal in regions of the heart located distally in the US path (e.g., 5-10 o'clock positions in the myocardium and adjacent LV cavity in the PSA view, FIG. 5A). As the circulating-bubble concentration in the blood pool (LV cavity) decreased over time, the attenuation diminished (compare frame 0:30 vs 6:20, FIG. 5A) but did not disappear (frame 20:20, FIG. 5A (1))—likely due to attenuation caused by overlying bone, lung air±retained-bubbles located proximally in the US path. Esel expression in the myocardium was visualised in real-time, indicated by the persistence of bubble signal (due to retained bubbles) in the WT myocardium as the freely circulating-bubbles in the blood pool (LV cavity) decreased and disappeared over time. In the KO myocardium, where Esel is absent, the persistence of bubble signal was low/minimal, consistent with a low/minimal degree of non-specific bubble retention in the myocardium, FIGS. 5A and 5B.

US attenuation caused by overlying bone, lung air±retained-bubbles located proximally in the US path, affected certain parts of the myocardium depending on the imaging scan plane—this caused pseudo-loss of targeted bubble signal for Esel in the WT animals (e.g., there was artefactual loss of retained-bubble signal in the mid-posterior, -inferior, -posteroseptal and -anteroseptal walls of the LV (anti-clockwise from 5-10 o'clock positions, respectively) in the PSA view with 14 MHz CPS imaging). However, by changing the scan plane (e.g., from PSA to PLA or A4C view) to alter the relative position of overlying entities, or by lowering the US frequency to increase its penetrative depth (e.g., from 14 to 7 MHz), these attenuation effects could be overcome with good recovery of the retained-bubble signals, FIG. 5B. The global expression of Esel in the WT myocardium was thus demonstrated on US imaging, consistent with the immunohistochemistry data.

In the above situation, US detection of molecular target was limited by late distal attenuation from overlying bone/air and retained-bubbles located proximally in the US path. However, it was found that such attenuation could be overcome by using lower frequency US (greater penetrative depth) or a different imaging angle. From the human imaging perspective, where the use of lower frequency US (e.g., 3-7 MHz) and multi-plane imaging are the norm, and the footprint of the transducer is much smaller relative to the body size (making it easier to achieve optimal probe position/angle and avoid overlying bone/air), these attenuation issues are likely less important/significant. Nevertheless, refinements in the machine's attenuation correction algorithm may further minimise the attenuation artefacts.

(3) Adverse Effects.

No death or significant adverse events attributable to the Esel targeting bubbles were observed. No significant bubble-medicated intravascular obstruction in the myocardium, causing loss of regional myocardial perfusion manifest as regional wall motion abnormality, was detected.

Ultrasound TIC of the Myocardium (Tissue) and LV Cavity (Central Blood Pool)

Three phases with distinct characteristics were discernable from the TICs following iv bolus administration of the targeting bubbles, FIG. 5A:

(1) Bolus-phase (B): lasting a few seconds, characterised by an initial rapid rise in bubble signal intensity reaching peak or saturating and/or attenuation levels (as bubble concentration increased) within seconds of bolus injection.

(2) Distribution-phase (D): lasting up to 1-2 min (takes a few circulatory cycles to complete), characterised by a short rapid decrease in bubble signal intensity, as bubbles dilute by mixing and distribution to tissues. High bubble concentration resulted in signal saturation and/or attenuation, obscuring re-circulation peaks. As the bubble concentration decreased further over time, the bubble signal intensity was frequently observed to paradoxically increase as attenuation decreased, giving rise to a second lower peak within 0.5-1 min of bubble administration (arrow in insets of FIG. 5A).

(3) Elimination-phase (E): lasting several minutes, characterised by a long slow decrease in bubble signal intensity. Bubble signal intensity in the LV cavity (representing freely circulating-bubble concentration in the central blood pool) became undetectable sooner in the WT than Esel KO animals; in both groups they were essentially undetectable by 20 min post bubble administration. In the myocardium, bubble signal intensity of WT animals decreased slower than that of KOs, and persisted beyond the disappearance of bubble signal in the LV cavity (due to the slower decay of retained bubbles (bubbles attached to Esel) in the myocardium compared with that of the freely circulating bubbles). In KO animals, bubble signal in the myocardium became undetectable before the disappearance of bubble signal in the LV cavity (as expected for fractional vascular volume of the heart or relative myocardial blood volume (rMBV)≤24%), except when a detectable degree of non-specific bubble retention was present.

Quantitative Analysis of US Imaging (1) Animals.

12 WT (age 5.7(mean)±0.3(SD) weeks, range 5.1-6.1 weeks; body weight 19.7(mean)±1.4(SD) g, range 18-22 g) and 8 Esel KO (age 7.9±3.2 weeks, range 5-13.6 weeks; body weight 22.3±3.7 g, range 17-28 g) mice were used. LPS$_{Time}$ ranged 3:53-5:59 h for the WT and 4:27-5:39 h for the KO group. Excluded from quantitative analysis here were 3 WT animals because of: (i) microbubble dosing error (1 animal); (ii) uncertainties regarding Esel expression level (2 animals); and (iii) 1 of these 3 animals has a TIC that could not be adequately quantified, possibly due to severe attenuation artefact.

(2) Acoustic Quantification of Esel Expression a. Prior-Art Method Based on Single Late Time Point Analysis.

Figure 7A:
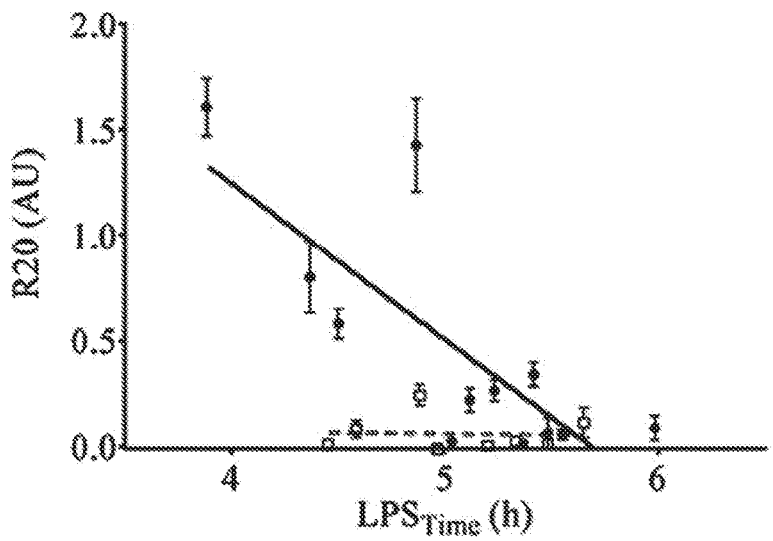
FIGS. 7A-7G are a series of graphs and table showing quantitative analysis of US imaging. Pearsons r.
Figure 7B:
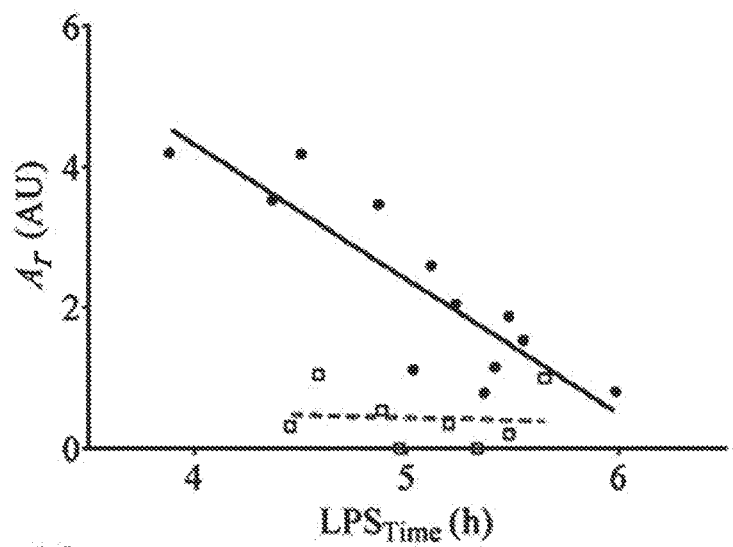
Figure 7C:
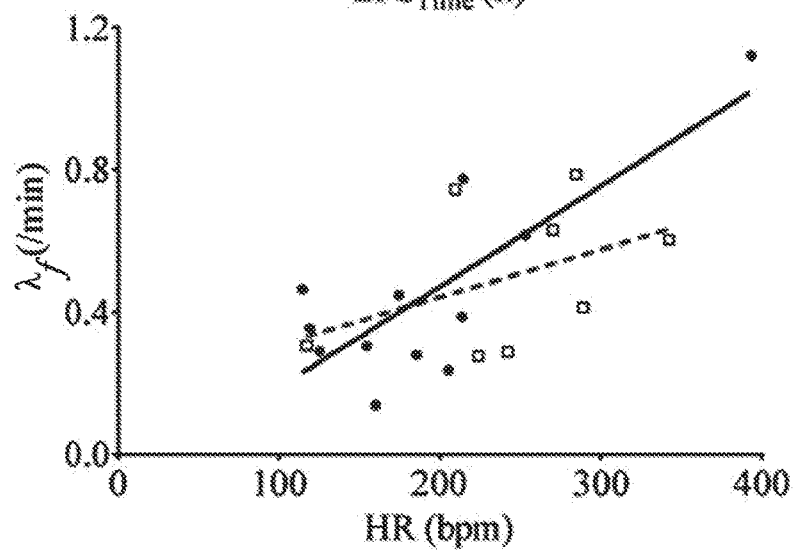
Figure 7D:
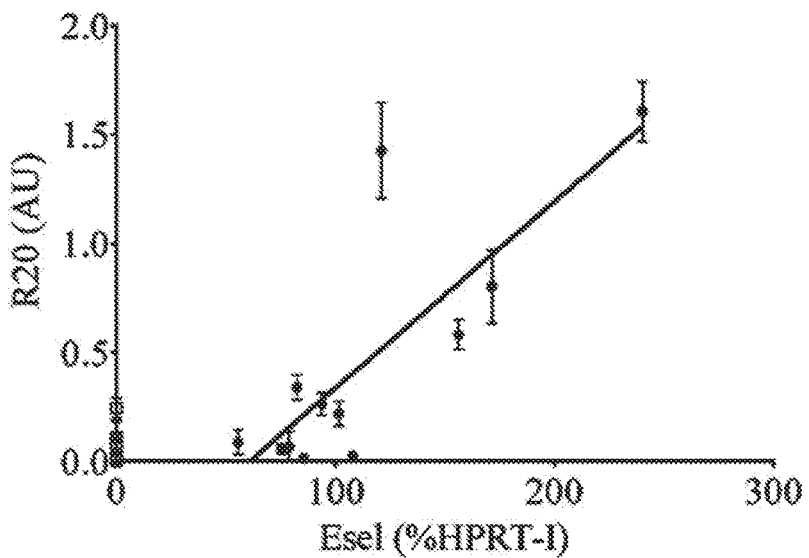

In both WT and Esel KO groups, freely circulating-bubble signal in the blood pool (LV cavity) was absent/minimal by following iv bolus administration of $10^8$ bubbles. Therefore, background-subtracted I in the myocardium at 20 min 10 s post bubble administration (R20) was used to represent that of the retained-bubbles only, as signal contribution from any residual freely circulating-bubbles by this time was considered negligible due to their low concentrations in the central blood pool (signal intensity in the LV cavity). E.g., 0.1AU in the LV cavity would contribute only 0.005-0.024AU in the myocardium assuming rMBV (% of myocardium that is blood) of ≤5-24%. R20 was significantly higher in the WT (0.46±0.16 (SEM), range 0.01-1.61, n=12) than KO (0.06±0.03, −0.01-0.24, n=8) animals, p<0.05 (FIG. 8). R20 correlated strongly with LPS$_{Time}$ in the WT (r=−0.78, p<0.05, n=12) but not KO mice (r=−0.05, p=0.9, n=8), FIG. 7A. It also correlated strongly with the concentration of Esel mRNA (r=0.81, p<0.005, n=12), FIG. 7D. However, at low target molecule (Esel) concentrations, R20 showed considerable overlap between the WT and KO groups and poor correlation with the target molecule concentration. R20 lacks sensitivity and low degree of quantification at low target molecule concentrations.

This prior-art method was poor at detecting low as well as small changes in the target molecule concentration. It is also prone to under-estimation when the target molecule concentrations are lower or the time point used is later. While I do not intend to be bound to any particular theory, I found that one reason for this may be that the method fails to take into account differences in the half-life of the retained-bubbles. The retained-bubble half-life decreased with decreased maximum retained-bubble concentration or decreased target molecule concentration (see $\lambda_r$ vs. $A_r$ below), and would be expected to decrease also with increased US insonation (due to increased US-mediated bubble deflation). These are important considerations because the target molecule concentration may be low in natural disease states, and variations in US exposure is common in practice. Furthermore, this method is prone to ambiguity—the value of the retained-bubble signal intensity (R value) at a single late-time point in the same subject would change if the time point chosen for measurement was changed (e.g., 20 min vs. 30 min post bubble administration). In summary, the prior-art method has a lower degree of quantification, is less accurate, less reproducible and more prone to ambiguity.

b. Bi-Exponential Curve Fit Method.

Figure 7E:
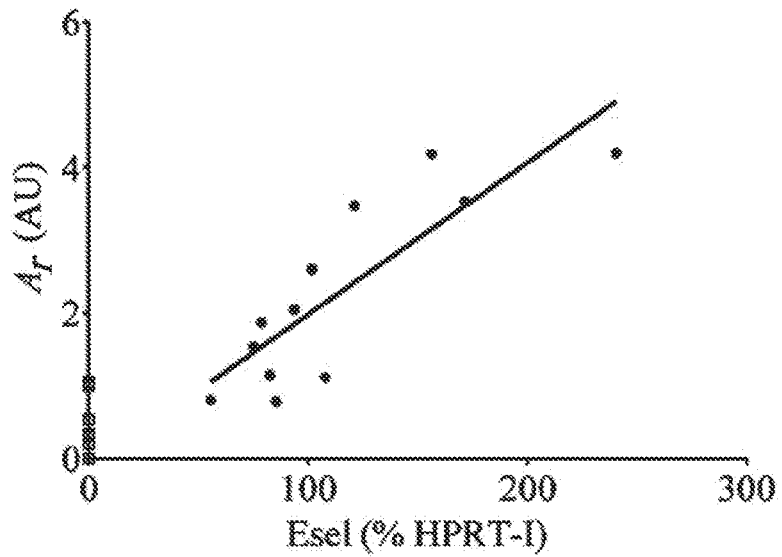

The elimination-phase TIC of the myocardium fitted well to $I(t)=A_f e^{-\lambda_f t}+A_r e^{-\lambda_r t}$ in both WT ($R^2$=0.88, n=12) and Esel KO animals ($R^2$=0.87, n=8), FIG. 8. The good curve fit suggested that the biexponential function predicted well the observed elimination-phase TIC of the targeting bubbles in vivo. The maximum retained-bubble signal intensity in the myocardium, $A_r$, was significantly higher in the WT (2.3±0.4 (SEM), range 0.8-4.2, n=12) than Esel KO (0.4±0.1, 0-1, n=8) animals, p<0.005. The low $A_r$ values in the KOs suggested minor degrees of non-specific bubble retention. $A_r$ correlated strongly with LPS$_{Time}$ in the WT (r=−0.87, p<0.0005, n=12) but not KO mice (r=−0.08, p=0.86, n=8), FIG. 7B . By converting LPS$_{Time}$ to the concentration of Esel mRNA using the curve in FIG. 4A, FIG. 7E showed that $A_r$ correlated strongly with the concentration of Esel mRNA (r=0.84, p<0.001, n=12), the latter in the range that was approximately linearly related to the concentration of the cell surface Esel protein (actual target of the microbubbles). At low target molecule (Esel) concentrations, $A_r$ showed minimal overlap between the WT and KO groups, and maintained a good correlation with the target molecule concentration.

Advantageously over the prior art, $A_r$ is more sensitive and has a higher degree of quantification. It is able to detect lower as well as smaller changes in the target molecule concentration. It is less prone to error. While I do not intend to be bound to any particular theory, I found that one reason for this may be that this method takes into account differences in the half-life of the retained-bubbles which varies with the retained-bubble or target molecule concentration, as well as degree of US exposure, as described above. These are important considerations because the target molecule concentration may be low in natural disease states, and variations in US exposure is common in practice. Furthermore, this method is less prone to ambiguity—there being only one value for $A_r$ from biexponential curve fit of each data set. In summary, the advantages of this method are that it has a higher degree of quantification, is more accurate, more reproducible, more robust and less unambiguous. It is also more amenable to standardisation. Simultaneously, other useful physical properties, such as the retained or freely circulating bubble half-life can be obtained simultaneously.

(3) Acoustic Quantification of Further Characteristics (from the Biexponential Curve-Fit Method)

a. Freely Circulating-Bubbles.

Figure 7F:
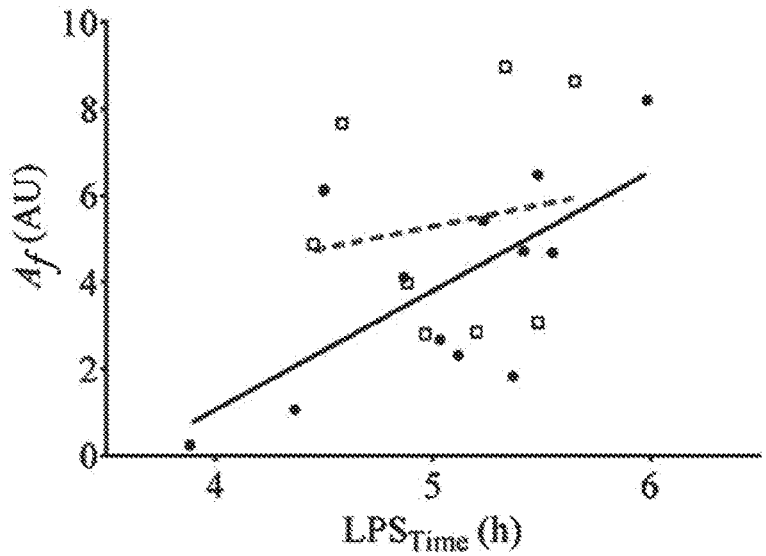

The elimination rate constants of freely circulating-bubbles in the myocardium ($\lambda_f$) of WT and KO animals in the elimination-phase were essentially the same, p=0.63 (FIG. 8). $\lambda_f$ correlated strongly with HR (FIG. 7C), consistent with increased clearance of freely circulating-bubbles due to HR-mediated increase in cardiac output (stroke volume×HR), delivering more bubbles per unit time to the acoustic field, reticuloendothelial system (e.g., liver and spleen) and lungs—major sites of bubble elimination. The half-life $$\left(\frac{Ln2}{\lambda_f}\right)$$

of the acoustically effective freely circulating-bubbles in vivo was ≈2(mean)±1(SD) min, range 1-5 min for the WT (n=12) and KO (n=8) animals. The maximum signal intensities, representing the maximum concentrations, of the freely circulating-bubbles in the myocardium ($A_f$) in the elimination-phase were lower in the WT than KO animals, although this did not reach statistical significance, FIG. 8. $A_f$ decreased with decreasing $LPS_{Time}$ in the WT but not KO animals, FIG. 7F, consistent with a decrease in freely circulating-bubble concentration with target-mediated bubble retention increases.

b. Retained-Bubbles.

$\lambda_r$ when compared with $\lambda_f$ showed that the half-lives of the retained-bubbles were generally longer (≥2-4×) than that of the freely circulating ones, consistent with the observed persistence of retained-bubble signal beyond that of the freely circulating ones. The half-life $$\left(\frac{Ln2}{\lambda_f}\right)$$

of the acoustically effective retained-bubbles in the myocardium was ≈7 (mean)±5(SD) min, range 3-18 min in the WT (n=12) compared with 4±4 min, range 1-14 min in the KO animals (n=8).

$\lambda_r$ vs. $A_r$.

Figure 7G:
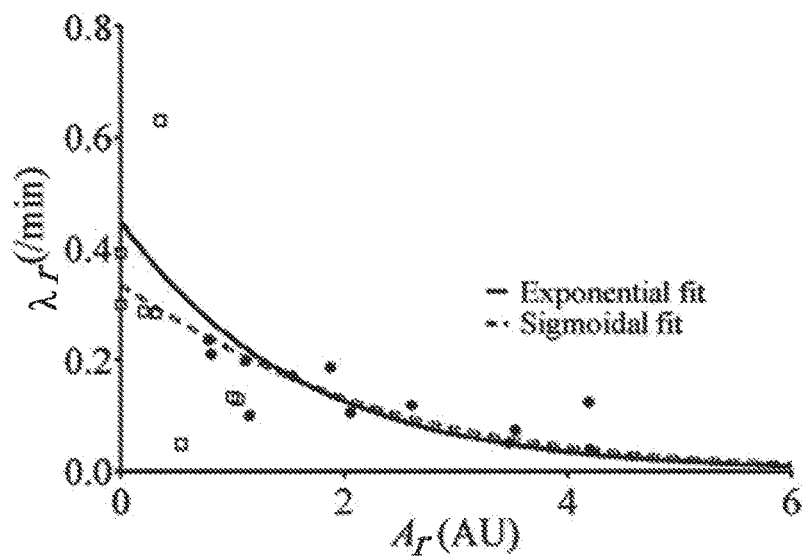

The elimination rate constant of the retained-bubbles in the myocardium ($\lambda_r$) decreased with increasing $A_r$, the latter representing the maximum concentration of retained-bubbles in the myocardium, FIG. 7G. The relationship was non-linear and could be empirically fitted to an exponential function ($\lambda_r=0.45\ e^{-0.64 A_r}$, $R^2=0.77$) or sigmoidal function $$\left(\lambda_r = \frac{1}{1 + 10^{(0.26 A_r + 0.3)}}, R^2 = 0.87\right),$$

n=12 WT & 8 KO. This suggested that the half-life of the retained-bubbles was shorter the lower the maximum retained-bubble concentration (the latter correlated with the target molecule concentration, see above). In another word, for the retained-bubbles in the elimination-phase, the higher their maximum concentration at the beginning when bubble accumulation at the target site was complete ($A_r$), the lower its elimination rate constant ($\lambda_r$) or the longer its half-life $$\left(\text{half-life} = \frac{Ln2}{\lambda_r}\right).$$

The relationship appeared non-linear. While I do not intend to be bound to any particular theory, I found that one reason for this may be that as the concentration of the retained-bubbles increases, the distance between neighbouring bubbles decreases, which may result in: (i) increased acoustical interaction between adjacent bubbles causing mechanical responses such that the net diffusion of gas out of the bubble population is reduced; and/or (ii) reduced concentration gradient for gas diffusion out of the bubbles due to increased gas saturated micro-environment surrounding the bubbles.

The videodensitometric method is used to process the US images. Above, it is described how a number of three seconds clips of images are acquired and recorded, and when they are processed, the corresponding images from each recorded clip are compared pixel by pixel or by region of interest so that signal intensities at those points of interest can be compared. Since the number of microbubbles reduces over time, the intensity of a point of interest will reduce over time. Different points of interest may behave differently with respect to the presence/absence/concentration of molecular target, flow and microparticle elimination characteristics, artifact (e.g., alignment/motion/machine/attenuation artifacts, which may/may not be intermittent). Using the bi-exponential function described above, the intensity detected in the images can be curve fitted so as to identify which bi-exponential curve fits best for each point. Once the curve is known, it is possible to obtain the parameters for the point of interest. $A_r$ indicates the maximum retained bubble concentration at the point of interest in the elimination phase. This process can be repeated for multiple points of interest across a region of interest. For each point of interest, pixels from each of a series of images are compared and then curve fitted. Once a number of points have been curve fitted, an average can be taken to obtain an accurate quantification of the values of the parameters for that region of interest. Alternatively, the averaging can be done before curve fitting takes place, averaging the intensities of the pixels in a particular image corresponding to a region of interest with a plurality of points of interest, and then comparing average intensity values for each image. The average values can then be curve fitted instead.

It will be appreciated that, for a particular point in the heart, the measured response for that point from an image taken at ≥three time points after for example ≈2-6 minute post bubble administration (e.g. at 2, 3 and 4 minutes or more time points; or at 4, 5 and 6 minutes or more time points; or at 6, 7 and 8 minutes or more time points; or at 7, 8 and 9 minutes or more time points post bubble administration) will give a series of values which can be fitted to a curve comprising a bi-exponential function:

$$I(t)=A_f e^{-\lambda_f t}+A_r e^{-\lambda_r t}$$

The part of the function: $A_f e^{-\lambda_f t}$ represents the elimination of free microbubbles, and the part of the function $A_r e^{-\lambda_r t}$ represents the elimination of retained microbubbles. The bi-exponential function predicts the elimination of free and retained microbubbles and allows the calculation of the concentration of retained and/or free microbubbles at any point.

Once the concentration of retained or free microbubbles for a series of points in a region of interest have been calculated, it is also possible to create an image to show the variation of these concentrations across that region of interest. Further, any of the other characteristics which can be derived from the curve could also be formed into an image, if desired. An image showing the variation of the half-life of the retained microbubbles within the region of interest might be formed, for example.

It will be appreciated that, since more than one image is collected, image processing takes place later because it requires a comparison to be carried out across the plurality of images that have been collected. Thus, the quantification takes place as a postprocessing operation.

Example

In another arrangement, it is possible to quantify characteristics even where contrast agents are not retained, for example in the blood pool of a heart cavity or blood vessel. For example, microbubbles can be administered and US imaging used, as described above, to take multiple images of a tissue and nearby blood pool (e.g, heart cavity or blood vessel). Points of interest in the tissue and nearby blood pool can be analysed, as described above, and the intensities curve fitted to the bi-exponential equation. In the blood pool, where microbubbles are not retained, the exponential term of the bi-exponential function relating to retained microbubbles will be zero or approach zero. The characteristics of the free microbubbles in the blood pool is determined from its respective exponential term. Further, the characteristics of free microbubbles within the tissue and free microbubbles within the blood pool can be compared to obtain useful information. For example, the ratio of tissue $A_f$ or tissue $AUC_f$ with that of the blood pool as the denominator allows one to obtain the fractional vascular volume of the tissue. Thus, an important clinical characteristic can be obtained using this method. Specifically, this method uniquely allows determination of the tissue fractional vascular volume using large bolus dose of microbubbles without imaging signal saturation and/or attenuation causing problems described above (works best when retained microbubble concentrations are minimal/low/moderate), in contrast to prior-art methods which require small (ie non-attenuating/saturating) microbubble dose to be used. Using this method also has advantages in quality control and data interpretation. For example, unexpected deviation of tissue $A_f$, $AUC_f$ or $\lambda_f$ from that of the blood pool may alert one to particular disease states such as circulatory obstruction; unexpected relationships amongst tissue $\lambda_f$, blood pool $\lambda_f$ and tissue $\lambda_r$ may alert one to anomalies in the US setting, bubbles or host.

Example

In another arrangement, the quantified characteristics can be obtained for non-targeting contrast agents or targeting contrast agents (the latter administered to a subject where the target molecule is known to be absent). In these situations, the contrast agent (depending on its nature) may be retained in a tissue/system due to non-specific mechanisms, such as (but not limited to) non-specific binding, non-specific cellular uptake, mechanical obstruction, or flow stasis. Here, the exponential term previously representing retained (targeted) contrast agent (as described above) can be used to represent non-specifically retained contrast agent in the analysis. Thus $A_r$ represents the degree of non-specific contrast agent retention in the tissue/system, which may be used to determine the dosage of contrast agent bearing therapeutic material being delivered to the tissue/system by non-specific retention.

FIG. 9 illustrates a system 100 used for implementing the method for quantifying the characteristics of an object using imaging as described herein.

The system 100 comprises an imaging system 110 and a data processing system 120. The imaging system 110, which may be a system such as an ultrasonic imaging system or an MRI system, is arranged to image an object 10. The imaging system 110 then sends captured image data to the data processing system 120. The data processing system 120 receives the captured image data at communications unit 121, which sends any data received from external systems to processor 122. The processor 122 then stores the received image data in memory 123. The processor 122 is then able to perform the various processes and analysis discussed throughout this document. The results of the processing performed by the processor 122 are then sent to a graphics card 124 for display on a monitor 20. The data processing system 120 also comprises a user interface module 125 arranged to receive instructions for controlling the operation of the data processing system 120 by a user via a user interface 30.

While the above system 100 is described as comprising a number of distinct components it will be appreciated that all of the components, or a subset of the components, shown in FIG. 9 may be integrated within a single unit. Furthermore, it will be appreciated that aspects of the system 100 may also be distributed components. For example, the processing may be performed by a distributed network of data processing systems. In addition, the processing may be carried out in a cloud computing environment.

The various methods described above may also be implemented by a computer program. In the system of FIG. 9, the computer program may be stored in memory 123 and executable by processor 122. The computer program may include computer code arranged to instruct a computer, such as the data processing system 120, to perform the functions of one or more of the various methods described above. The computer program and/or the code for performing such methods may be provided to an apparatus, such as a computer, on a computer readable medium or computer program product. The computer readable medium could be, for example, an electronic, magnetic, optical, electromagnetic, infrared, or semiconductor system, or a propagation medium for data transmission, for example for downloading the code over the Internet. Alternatively, the computer readable medium could take the form of a physical computer readable medium such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

The invention claimed is:

1. A method of quantifying the characteristics of an object using imaging, the object treated with a contrast agent, comprising:
   (a) receiving, from an imaging system, a plurality of imaging signals of the object captured over a period of time;
   (b) measuring, at a data processing system, the signal intensity in each of the plurality of imaging signals corresponding to a point on the object;
   (c) curve fitting, at the data processing system, the measured signal intensity of the point on the object to a bi-exponential function comprising a first and a second exponential term, the first exponential term representing the decrease in concentration of the contrast agent which is free over time and the second exponential term representing a decrease in concentration of the contrast agent which is retained on the object over time.

2. The method according to claim 1, further comprising the step of: creating an image comprising the quantified characteristic for at least a part of the object.

3. The method according to claim 1, further comprising capturing the plurality of imaging signals of the object over a period of time.

4. The method according to claim 3, wherein the plurality of imaging signals are captured once the concentration of contrast agent is less than the point where attenuation and/or saturation of the signal intensity is significant.

5. The method according to claim 1, further comprising the steps:
   (d) repeating steps (b) & (c) for points across a region of interest of the object; and
   (e) averaging the quantified characteristic.

6. The method according to claim 1, further comprising the steps:
   (d) repeating step (b) for points across a region of interest of the object;
   (e) averaging the signal intensities of points across the region of interest at particular times; and
   (f) carrying step (c) out on the average intensities.

7. The method according to claim 3, wherein the plurality of imaging signals captured over a period of time is a plurality of images.

8. The method according to claim 1, wherein the signal intensity measured in each of the plurality of imaging signals is the intensity of a pixel of each of the images which corresponds to the point on the object.

9. The method according to claim 1, where a videodensitometric method is used to process the images.

10. The method according to claim 1, wherein the bi-exponential function comprises:

$$I(t) = A_f e^{-\lambda_f t} + A_r e^{-\lambda_r t}$$

where I is the detected signal intensity representing contrast agent concentration, $A_f$ represents the maximum concentration of the free contrast agent in the elimination phase, $A_r$ represents the maximum concentration of the retained contrast agent in the elimination phase, $\lambda_r$ is the elimination rate constant for the retained contrast agent and $\lambda_f$ is the elimination rate constant for the free contrast agent, and t is time after termination of contrast agent administration.

11. The method according to claim 1, wherein the biexponential equation further comprises one or more components selected from a list comprising constant, scaling factor, factor, exponential term.

12. The method according to claim 10, further comprising quantifying, at the data processing system, the characteristic of the maximum concentration $A_r$, of retained contrast agent.

13. The method according to claim 10, further comprising quantifying, at the data processing system, the characteristic of the elimination rate constant $\lambda_r$ of retained contrast agent.

14. The method according to claim 1, further comprising quantifying, at the data processing system, the characteristic of the half-life of retained contrast agent.

15. The method according to claim 10, further comprising quantifying, at the data processing system, the characteristic of the concentration $A_r e^{-\lambda_r t}$ of retained contrast agent.

16. The method according to claim 1, further comprising quantifying, at the data processing system, the characteristic of an area under curve of retained contrast agent.

17. The method according to claim 10, further comprising quantifying, at the data processing system, the characteristic of the elimination rate constant $\lambda_f$ free contrast agent.

18. The method according to claim 1, further comprising quantifying, at the data processing system, the characteristic of the half-life of free contrast agent.

19. The method according to claim 10, further comprising quantifying, at the data processing system, the characteristic of the maximum concentration $A_f$ of free contrast agent.

20. The method according to claim 1, further comprising quantifying, at the data processing system, the characteristic of the concentration $A_f e^{-ft}$ of free contrast agent.

21. The method according to claim 1, further comprising quantifying, at the data processing system, the characteristic of an area under curve of free contrast agent.

22. The method according to claim 1, further comprising quantifying, at the data processing system, the fractional vascular volume of a tissue, by taking the ratio of $A_f$ or $AUC_f$ from two regions of interest, the denominator being that for the region of interest placed in a blood pool region.

23. The method according to claim 1, wherein the contrast agent is a plurality of microbubbles with or without molecular binding elements.

24. The method according to claim 1, wherein imaging is ultrasonic imaging.

25. The method according to claim 1, wherein imaging is magnetic resonance imaging.

26. A system for quantifying the characteristics of an object using imaging, the object treated with a contrast agent, comprising a data processing system having:
   a communications unit configured to receive a plurality of imaging signals of the object captured over a period of time; and
   a processor configured to:
      (i) measure the signal intensity in each of the imaging signals corresponding to a point on the object; and
      (ii) curve fit the measured signal intensities of the point on the object to a bi-exponential function comprising a first and a second exponential term, the first exponential term representing the decrease in concentration of the contrast agent which is free over time and the second exponential term representing a decrease in concentration of the contrast agent which is retained on the object over time.

27. The system according to claim 26, further comprising an imaging system arranged to capture the plurality of imaging signals of the object over the period of time.

28. Apparatus for quantifying the characteristics of an object using imaging, the object treated with a contrast agent, wherein the apparatus comprises a data processing system having a communications unit and a processor, the data processing system configured to carry out the method of:
   (a) receiving at the communications unit, from an imaging system, a plurality of imaging signals of the object captured over a period of time;
   (b) measuring at the processor of the data processing system, the signal intensity in each of the plurality of imaging signals corresponding to a point on the object;
   (c) curve fitting at the processor of the data processing system, the measured signal intensity of the point on the object to a bi-exponential function comprising a first and a second exponential term, the first exponential term representing the decrease in concentration of the contrast agent which is free over time and the second exponential term representing a decrease in concentration of the contrast agent which is retained on the object over time.

29. A computer program stored on a non-transitory computer-readable medium, the computer program comprising computer readable code which is operable in use to instruct a computer to perform the method of:
   (a) receiving, from an imaging system, a plurality of imaging signals of the object captured over a period of time;
   (b) measuring, at a data processing system, the signal intensity in each of the plurality of imaging signals corresponding to a point on the object; and
   (c) curve fitting, at the data processing system, the measured signal intensity of the point on the object to a bi-exponential function comprising a first and a second exponential term, the first exponential term representing the decrease in concentration of the contrast agent which is free over time and the second exponential term representing a decrease in concentration of the contrast agent which is retained on the object over time.

30. A non-transitory computer readable medium comprising computer program code which operable in use to instruct a computer to perform the method of:
   (a) receiving, from an imaging system, a plurality of imaging signals of the object captured over a period of time;
   (b) measuring, at a data processing system, the signal intensity in each of the plurality of imaging signals corresponding to a point on the object;
   (c) curve fitting, at the data processing system, the measured signal intensity of the point on the object to a bi-exponential function comprising a first and a second exponential term, the first exponential term representing the decrease in concentration of the contrast agent which is free over time and the second exponential term representing a decrease in concentration of the contrast agent which is retained on the object over time.

* * * * *

SEQUENCE LISTING

<160> NUMBER OF SEQ ID NOS: 4

<210> SEQ ID NO 1
<211> LENGTH: 22
<212> TYPE: DNA
<213> ORGANISM: Artificial sequence
<220> FEATURE:
<223> OTHER INFORMATION: Esel forward primer

<400> SEQUENCE: 1
ctcattgctc tacttgttga tg                    22

<210> SEQ ID NO 2
<211> LENGTH: 19
<212> TYPE: DNA

```
<213> ORGANISM: Artificial sequence
<220> FEATURE:
<223> OTHER INFORMATION: Esel reverse primer

<400> SEQUENCE: 2
gcatttgtgt tcctgattg                                            19

<210> SEQ ID NO 3
<211> LENGTH: 19
<212> TYPE: DNA
<213> ORGANISM: Artificial sequence
<220> FEATURE:
<223> OTHER INFORMATION: HPRT-1 forward primer

<400> SEQUENCE: 3
attagcgatg atgaaccag                                            19

<210> SEQ ID NO 4
<211> LENGTH: 20
<212> TYPE: DNA
<213> ORGANISM: Artificial sequence
<220> FEATURE:
<223> OTHER INFORMATION: HPRT-1 reverse primer

<400> SEQUENCE: 4
agtctttcag tcctgtccat                                           20
```